(12) United States Patent
Hellendoorn et al.

(10) Patent No.: US 7,524,502 B2
(45) Date of Patent: Apr. 28, 2009

(54) MODIFIED ANTI-TNF ALPHA ANTIBODY

(75) Inventors: Koen Hellendoorn, Newmarket (GB);
Matthew Baker, Cambridge (GB);
Francis J. Carr, Aberdeenshire (GB)

(73) Assignee: Merck Patent GmbH, Darmstadt (DE)

( * ) Notice: Subject to any disclaimer, the term of this patent is extended or adjusted under 35 U.S.C. 154(b) by 719 days.

(21) Appl. No.: 10/495,146

(22) PCT Filed: Nov. 11, 2002

(86) PCT No.: PCT/EP02/12566

§ 371 (c)(1),
(2), (4) Date: May 10, 2004

(87) PCT Pub. No.: WO03/042247

PCT Pub. Date: May 22, 2003

(65) Prior Publication Data

US 2004/0260069 A1   Dec. 23, 2004

(30) Foreign Application Priority Data

Nov. 12, 2001   (EP)   ................... 01126858

(51) Int. Cl.
*A61K 39/395* (2006.01)
(52) U.S. Cl. ................. 424/158.1; 530/388.23
(58) Field of Classification Search .............. None
See application file for complete search history.

(56) References Cited

U.S. PATENT DOCUMENTS 5,712,120 A * 1/1998 Rodriguez et al. ......... 435/69.6
5,919,452 A * 7/1999 Le et al. .................. 424/133.1

OTHER PUBLICATIONS

Deavin et al., Mol Immunol. Feb. 1996;33(2):145-55.*
Mateo et al., Hybridoma. Dec. 2000;19(6):463-71.*
Harold Chapman, Current Opinion in Immunology 1998, 10:93-102.*
Janeway et al., Immunobiology, 5th Ed., Garland Science, pp. 94-105 (2001).*
Vajdos et al., J Mol Biol. Jul. 5, 2002;320(2):415-28.*
Rudikoff et al, Proc. Natl. Acad. Sci. USA, 79:1979-1883, Mar. 1982.*
Colman P. M., Research in Immunology, 145:33-36, 1994.*

* cited by examiner

*Primary Examiner*—Michail A Belyavskyi
*Assistant Examiner*—Zachary Skelding
(74) *Attorney, Agent, or Firm*—Olson & Cepuritis, Ltd.

(57) ABSTRACT

The invention relates to the modification of antibodies reactive to human tumor necrosis factor alpha (TNF alpha) to result in anti-TNF alpha antibodies that are substantially non-immunogenic or less immunogenic than any non-modified parental antibody when used in vivo. The invention relates also to peptide molecules comprising T-cell epitopes of the V-regions of the parental antibody which are modified by amino acid alteration in order to reduce or eliminate said T-cell epitopes.

4 Claims, 10 Drawing Sheets

FIGURE 1

FIG. 1A

Figure 2:
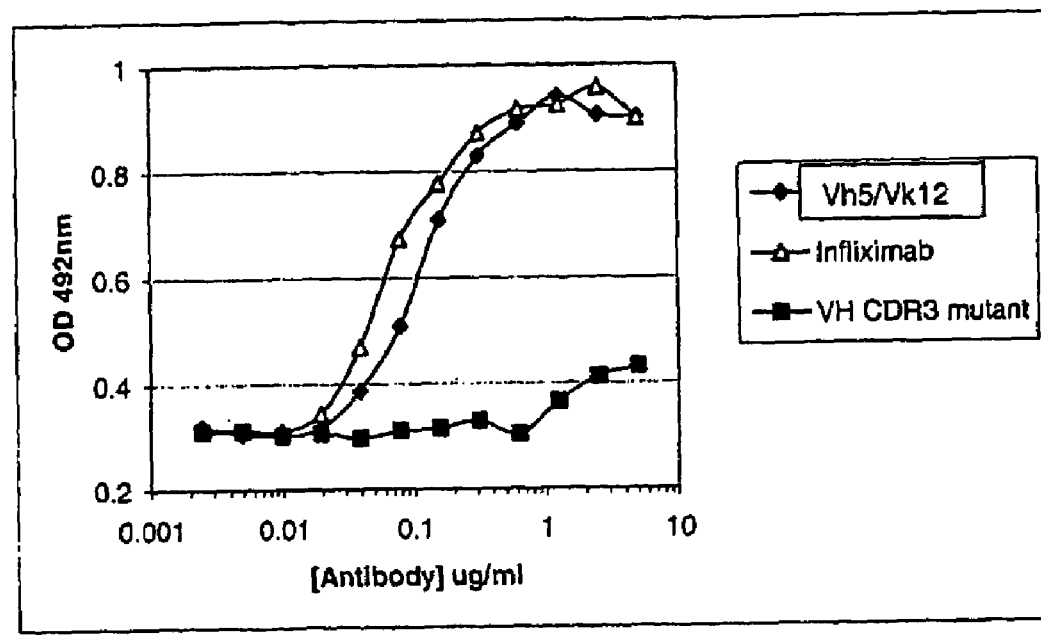

Peptide sequences from heavy chain variable region of anti-TNFα antibody A2 with potential human MHC class II binding activity.

SEQ ID NO: is listed in parenthesis after sequence:

| | | |
|---|---|---|
| VKLEESGGGLVQP (180) | GGLVQPGGSMKLS (181) | GLVQPGGSMKLSC (182) |
| GSMKLSCVASGFI (183) | MKLSCVASGFIFS (184) | SCVASGFIFSNHW (185) |
| SGFIFSNHWMNWV (186) | GFIFSNHWMNWVR (187) | FIFSNHWMNWVRQ (188) |
| NHWMNWVRQSPEK (189) | HWMNWVRQSPEKG (190) | MNWVRQSPEKGLE (191) |
| NWVRQSPEKGLEW (192) | KGLEWVAEIRSKS (92) | LEWVAEIRSKSIN (193) |
| EWVAEIRSKSINS (93) | AEIRSKSINSATH (94) | KSINSATHYAESV (95) |
| THYAESVKGRFTI (194) | ESVKGRFTISRDD (195) | GRFTISRDDSKSA (196) |
| FTISRDDSKSAVY (197) | SAVYLQMTDLRTE (198) | AVYLQMTDLRTED (199) |
| VYLQMTDLRTEDT (200) | LQMTDLRTEDTGV (201) | TDLRTEDTGVYYC (202) |
| TGVYYCSRNYYGS (96) | GVYYCSRNYYGST (203) | VYYCSRNYYGSTY (204) |
| RNYYGSTYDYWGQ (205) | NYYGSTYDYWGQG (206) | STYDYWGQGTTLT (97) |
| YDWGQGTTLTVS (207) | | |

FIG. 1B

Peptide sequences from light chain variable region of anti-TNFα antibody A2 with potential human MHC class II binding activity.

SEQ ID NO: is listed in parenthesis after sequence:

| | | |
|---|---|---|
| DILLTQSPAILSV (208) | ILLTQSPAILSVS (209) | PAILSVSPGERVS (210) |
| AILSVSPGERVSF (211) | LSVSPGERVSFSC (212) | ERVSFSCRASQFV (213) |
| VSFSCRASQFVGS (214) | SQFVGSSIHWYQQ (98) | QFVGSSIHWYQQR (99) |
| SSIHWYQQRTNGS (100) | IHWYQQRTNGSPR (215) | HWYQQRTNGSPRL (101) |
| PRLLIKYASESMS (102) | RLLIKYASESMSG (103) | LLIKYASESMSGI (104) |
| IKYASESMSGIPS (105) | ESMSGIPSRFSGS (106) | SGIPSRFSGSGSG (216) |
| SRFSGSGSGTDFT (217) | TDFTLSINTVESE (218) | FTLSINTVESEDI (219) |
| LSINTVESEDIAD (220) | NTVESEDIADYYC (221) | EDIADYYCQQSHS (222) |
| ADYYCQQSHSWPF (223) | DYYCQQSHSWPFT (224) | HSWPFTFGSGTNL (225) |
| WPFTFGSGTNLEV (226) | | |

Peptides are 13mers, amino acid are identified using single letter codes.

Neutralisation of the TNFα induced killing of WEHI164 cells

Neutralisation of the TNFα stimulated production of ICAM-1 in HUVE cells

Competition with TNF-receptor for binding TNFα

FIGURE 6
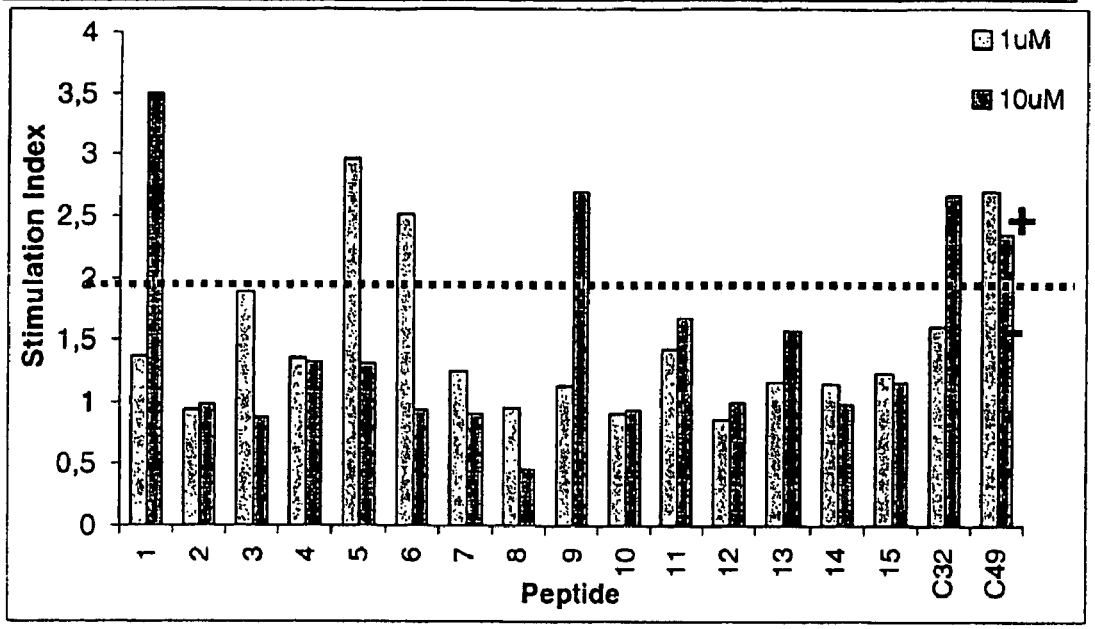
A) Donor #2 response to stimulation with peptides P1-P15
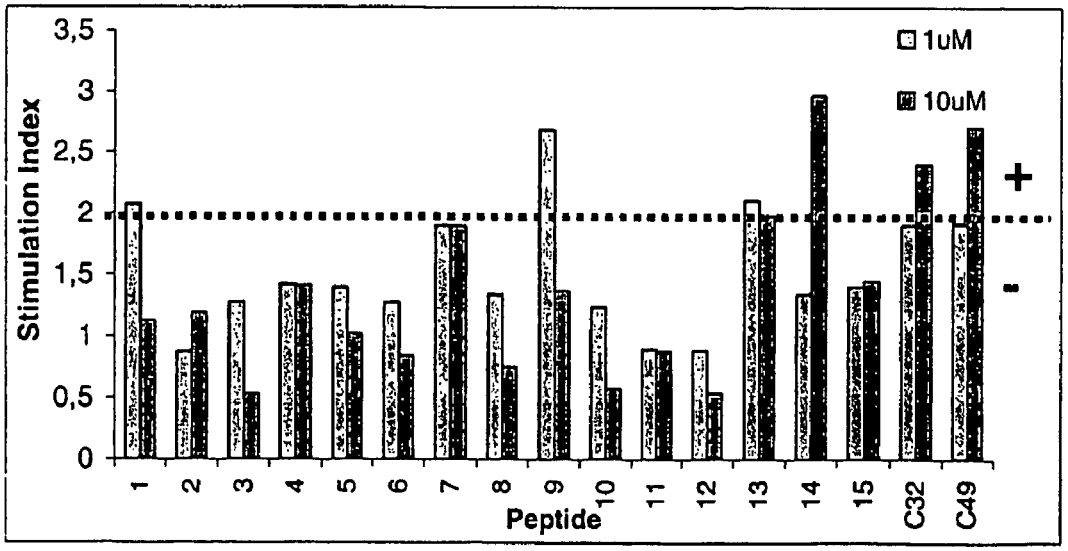
B) Donor #4 response to stimulation with peptides P1-P15

FIGURE 8

Vh1 (SEQ ID 1)
EVQLVESGGGLVQPGGSLRLSCAASGFTFSNHWMNWVRQSPEKGLEWVAEIRSKS
INSATHYAESVKGRFTISRDDSKNSLYLQMNSLKTEDTAVYYCSRNYYGSTYDYW
GQGTTLTVSS

Vh3 (SEQ ID 2)
EVKLEESGGGLVQPGGSLRLSCAASGFTFSNHWMNWVRQSPEKGLEWVAEIRSKS
INSATHYAESVKGRFTISRDDSKNSLYLQMNSLKTEDTGVYYCSRNYYGSTYDYW
GQGTTVTVSS

Vh5 (SEQ ID 3)
EVKLEESGGGLVQPGGSLRLSCAASGFTFSNHWMNWVRQSPEKGLEWVAETRSKS
TNSATHYAESVKGRFTISRDDSKNSLYLQMNSLKTEDTGVYYCSRNYYGSTYDYW
GQGTTVTVSS

Vh8 (SEQ ID 4)
EVQLVESGGGLVQPGGSLRLSCAASGFTFSNHWMNWVRQSPEKGLEWVAETRSKS
TNSATHYADSVKGRFTISRDDSKNSLYLQMNSLKTEDTAVYYCSRNYYGSTYDYW
GQGTLVTVSS

Vk1 (SEQ ID 5)
DIQLTQSPDTSSASPGERVSFSCRASQFVGSSIHWYQQRTNGSPRLLIKYASESM
SGVPSRFSGSGSGTDFTLTINSLEAEDAATYYCQQSHSWPFTFGSGTNVEVKR

Vk12 (SEQ ID 6)
DIQLTQSPDTSSASPGERASFSCRASQFVGSSIHWYQHTTNGSPRLLIKYASESM
SGVPSRFSGSGSGTDFTLTINSLEAEDAATYYCQQSHSWPFTFGSGTNLEVKR

Vk5 (SEQ ID 7)
DIQLTQSPDTSSASPGERVSFSCRASQFVGSSIHWYQQRTNGSPRLLIKYASESM
SGVPSRFSGSGSGTDFTLTINSLEAEDAATYYCQQSHSWPFTFGGGTKVEIKR

Vk8 (SEQ ID 8)
DIQLTQSPDTSSASPGERASFSCRASQFVGSSIHWYQHTTNGSPRLLIKYASESM
SGVPSRFSGSGSGTDFTLTINSLEAEDAATYYCQQSHSWPFTFGGGTKVEIKR

SEQUENCE LISTING

<160> NUMBER OF SEQ ID NOS: 226

<210> SEQ ID NO 1
<211> LENGTH: 120
<212> TYPE: PRT
<213> ORGANISM: mus musculus

<400> SEQUENCE: 1

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120

<210> SEQ ID NO 2
<211> LENGTH: 120
<212> TYPE: PRT
<213> ORGANISM: mus musculus

<400> SEQUENCE: 2

Glu Val Lys Leu Glu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Val Thr Val Ser Ser
        115                 120

<210> SEQ ID NO 3
<211> LENGTH: 120
<212> TYPE: PRT
<213> ORGANISM: mus musculus

<400> SEQUENCE: 3

```
Glu Val Lys Leu Glu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45

Ala Glu Thr Arg Ser Lys Ser Thr Asn Ser Ala Thr His Tyr Ala Glu
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Gly Val Tyr
                 85                  90                  95

Tyr Cys Ser Arg Asn Tyr Tyr Gly Ser Thr Tyr Asp Tyr Trp Gly Gln
                100                 105                 110

Gly Thr Thr Val Thr Val Ser Ser
            115                 120
```

<210> SEQ ID NO 4
<211> LENGTH: 120
<212> TYPE: PRT
<213> ORGANISM: mus musculus

<400> SEQUENCE: 4

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45

Ala Glu Thr Arg Ser Lys Ser Thr Asn Ser Ala Thr His Tyr Ala Asp
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
                100                 105                 110

Gly Thr Leu Val Thr Val Ser Ser
            115                 120
```

<210> SEQ ID NO 5
<211> LENGTH: 108
<212> TYPE: PRT
<213> ORGANISM: mus musculus

<400> SEQUENCE: 5

```
Asp Ile Gln Leu Thr Gln Ser Pro Asp Thr Ser Ser Ala Ser Pro Gly
  1               5                  10                  15

Glu Arg Val Ser Phe Ser Cys Arg Ala Ser Gln Phe Val Gly Ser Ser
             20                  25                  30

Ile His Trp Tyr Gln Gln Arg Thr Asn Gly Ser Pro Arg Leu Leu Ile
         35                  40                  45

Lys Tyr Ala Ser Glu Ser Met Ser Gly Val Pro Ser Arg Phe Ser Gly
     50                  55                  60
```

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Ser Gly Thr Asn Val Glu Val Lys Arg
            100                 105
```

<210> SEQ ID NO 6
<211> LENGTH: 108
<212> TYPE: PRT
<213> ORGANISM: mus musculus

<400> SEQUENCE: 6

```
Asp Ile Gln Leu Thr Gln Ser Pro Asp Thr Ser Ser Ala Ser Pro Gly
 1               5                  10                  15

Glu Arg Ala Ser Phe Ser Cys Arg Ala Ser Gln Phe Val Gly Ser Ser
                 20                  25                  30

Ile His Trp Tyr Gln His Thr Thr Asn Gly Ser Pro Arg Leu Leu Ile
             35                  40                  45

Lys Tyr Ala Ser Glu Ser Met Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Ser Gly Thr Asn Leu Glu Val Lys Arg
            100                 105
```

<210> SEQ ID NO 7
<211> LENGTH: 108
<212> TYPE: PRT
<213> ORGANISM: mus musculus

<400> SEQUENCE: 7

```
Asp Ile Gln Leu Thr Gln Ser Pro Asp Thr Ser Ser Ala Ser Pro Gly
 1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Gly Gly Thr Lys Val Glu Ile Lys Arg
            100                 105
```

<210> SEQ ID NO 8
<211> LENGTH: 108
<212> TYPE: PRT
<213> ORGANISM: mus musculus

<400> SEQUENCE: 8

Asp Ile Gln Leu Thr Gln Ser Pro Asp Thr Ser Ser Ala Ser Pro Gly
1               5                   10                  15

Glu Arg Ala Ser Phe Ser Cys Arg Ala Ser Gln Phe Val Gly Ser Ser
            20                  25                  30

Ile His Trp Tyr Gln His Thr Thr Asn Gly Ser Pro Arg Leu Leu Ile
        35                  40                  45

Lys Tyr Ala Ser Glu Ser Met Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Gly Gly Thr Lys Val Glu Ile Lys Arg
            100                 105

<210> SEQ ID NO 9
<211> LENGTH: 16
<212> TYPE: PRT
<213> ORGANISM: mus musculus

<400> SEQUENCE: 9

Gly Leu Val Gln Pro Gly Gly Ser Met Lys Leu Ser Cys Val Ala Ser
1               5                   10                  15

<210> SEQ ID NO 10
<211> LENGTH: 13
<212> TYPE: PRT
<213> ORGANISM: mus musculus

<400> SEQUENCE: 10

Trp Val Ala Glu Ile Arg Ser Lys Ser Ile Asn Ser Ala
1               5                   10

<210> SEQ ID NO 11
<211> LENGTH: 18
<212> TYPE: PRT
<213> ORGANISM: mus musculus

<400> SEQUENCE: 11

Ser Arg Asp Asp Ser Lys Ser Ala Val Tyr Leu Gln Met Thr Asp Leu
1               5                   10                  15

Arg Thr

<210> SEQ ID NO 12
<211> LENGTH: 21
<212> TYPE: PRT
<213> ORGANISM: mus musculus

<400> SEQUENCE: 12

Arg Asn Tyr Tyr Gly Ser Thr Tyr Asp Tyr Trp Gly Gln Gly Thr Thr
1               5                   10                  15

Leu Thr Val Ser Ser
            20

<210> SEQ ID NO 13
<211> LENGTH: 21
<212> TYPE: PRT
<213> ORGANISM: mus musculus -continued

```
<400> SEQUENCE: 13

Asp Ile Leu Leu Thr Gln Ser Pro Ala Ile Leu Ser Val Ser Pro Gly
1               5                   10                  15

Glu Arg Val Ser Phe
            20

<210> SEQ ID NO 14
<211> LENGTH: 12
<212> TYPE: PRT
<213> ORGANISM: mus musculus

<400> SEQUENCE: 14

His Trp Tyr Gln Gln Arg Thr Asn Gly Ser Pro Arg
1               5                   10

<210> SEQ ID NO 15
<211> LENGTH: 14
<212> TYPE: PRT
<213> ORGANISM: mus musculus

<400> SEQUENCE: 15

Leu Ile Lys Tyr Ala Ser Glu Ser Met Ser Gly Ile Pro Ser
1               5                   10

<210> SEQ ID NO 16
<211> LENGTH: 21
<212> TYPE: PRT
<213> ORGANISM: mus musculus

<400> SEQUENCE: 16

Asp Phe Thr Leu Ser Ile Asn Thr Val Glu Ser Glu Asp Ile Ala Asp
1               5                   10                  15

Tyr Tyr Cys Gln Gln
            20

<210> SEQ ID NO 17
<211> LENGTH: 15
<212> TYPE: PRT
<213> ORGANISM: mus musculus

<400> SEQUENCE: 17

Glu Val Lys Leu Glu Glu Ser Gly Gly Gly Leu Val Gln Pro Gly
1               5                   10                  15

<210> SEQ ID NO 18
<211> LENGTH: 15
<212> TYPE: PRT
<213> ORGANISM: mus musculus

<400> SEQUENCE: 18

Leu Glu Glu Ser Gly Gly Gly Leu Val Gln Pro Gly Gly Ser Met
1               5                   10                  15

<210> SEQ ID NO 19
<211> LENGTH: 15
<212> TYPE: PRT
```

<400> SEQUENCE: 19

Ser Gly Gly Gly Leu Val Gln Pro Gly Gly Ser Met Lys Leu Ser
1               5                   10                  15

<210> SEQ ID NO 20
<211> LENGTH: 15
<212> TYPE: PRT
<213> ORGANISM: mus musculus

<400> SEQUENCE: 20

Gly Leu Val Gln Pro Gly Gly Ser Met Lys Leu Ser Cys Val Ala
1               5                   10                  15

<210> SEQ ID NO 21
<211> LENGTH: 15
<212> TYPE: PRT
<213> ORGANISM: mus musculus

<400> SEQUENCE: 21

Gln Pro Gly Gly Ser Met Lys Leu Ser Cys Val Ala Ser Gly Phe
1               5                   10                  15

<210> SEQ ID NO 22
<211> LENGTH: 15
<212> TYPE: PRT
<213> ORGANISM: mus musculus

<400> SEQUENCE: 22

Gly Ser Met Lys Leu Ser Cys Val Ala Ser Gly Phe Ile Phe Ser
1               5                   10                  15

<210> SEQ ID NO 23
<211> LENGTH: 15
<212> TYPE: PRT
<213> ORGANISM: mus musculus

<400> SEQUENCE: 23

Lys Leu Ser Cys Val Ala Ser Gly Phe Ile Phe Ser Asn His Trp
1               5                   10                  15

<210> SEQ ID NO 24
<211> LENGTH: 15
<212> TYPE: PRT
<213> ORGANISM: mus musculus

<400> SEQUENCE: 24

Cys Val Ala Ser Gly Phe Ile Phe Ser Asn His Trp Met Asn Trp
1               5                   10                  15

<210> SEQ ID NO 25
<211> LENGTH: 15
<212> TYPE: PRT
<213> ORGANISM: mus musculus

<400> SEQUENCE: 25

Ser Gly Phe Ile Phe Ser Asn His Trp Met Asn Trp Val Arg Gln
1               5                   10                  15

<210> SEQ ID NO 26
<211> LENGTH: 15
<212> TYPE: PRT
<213> ORGANISM: mus musculus

```
<400> SEQUENCE: 26

Ile Phe Ser Asn His Trp Met Asn Trp Val Arg Gln Ser Pro Glu
 1               5                  10                  15

<210> SEQ ID NO 27
<211> LENGTH: 15
<212> TYPE: PRT
<213> ORGANISM: mus musculus

<400> SEQUENCE: 27

Asn His Trp Met Asn Trp Val Arg Gln Ser Pro Glu Lys Gly Leu
 1               5                  10                  15

<210> SEQ ID NO 28
<211> LENGTH: 15
<212> TYPE: PRT
<213> ORGANISM: mus musculus

<400> SEQUENCE: 28

Met Asn Trp Val Arg Gln Ser Pro Glu Lys Gly Leu Glu Trp Val
 1               5                  10                  15

<210> SEQ ID NO 29
<211> LENGTH: 15
<212> TYPE: PRT
<213> ORGANISM: mus musculus

<400> SEQUENCE: 29

Val Arg Gln Ser Pro Glu Lys Gly Leu Glu Trp Val Ala Glu Ile
 1               5                  10                  15

<210> SEQ ID NO 30
<211> LENGTH: 15
<212> TYPE: PRT
<213> ORGANISM: mus musculus

<400> SEQUENCE: 30

Ser Pro Glu Lys Gly Leu Glu Trp Val Ala Glu Ile Arg Ser Lys
 1               5                  10                  15

<210> SEQ ID NO 31
<211> LENGTH: 15
<212> TYPE: PRT
<213> ORGANISM: mus musculus

<400> SEQUENCE: 31

Lys Gly Leu Glu Trp Val Ala Glu Ile Arg Ser Lys Ser Ile Asn
 1               5                  10                  15

<210> SEQ ID NO 32
<211> LENGTH: 15
<212> TYPE: PRT
<213> ORGANISM: mus musculus

<400> SEQUENCE: 32

Glu Trp Val Ala Glu Ile Arg Ser Lys Ser Ile Asn Ser Ala Thr
 1               5                  10                  15

<210> SEQ ID NO 33
<211> LENGTH: 15
<212> TYPE: PRT
<213> ORGANISM: mus musculus
```

```
<400> SEQUENCE: 33

Ala Glu Ile Arg Ser Lys Ser Ile Asn Ser Ala Thr His Tyr Ala
 1               5                  10                  15

<210> SEQ ID NO 34
<211> LENGTH: 15
<212> TYPE: PRT
<213> ORGANISM: mus musculus

<400> SEQUENCE: 34

Arg Ser Lys Ser Ile Asn Ser Ala Thr His Tyr Ala Glu Ser Val
 1               5                  10                  15

<210> SEQ ID NO 35
<211> LENGTH: 15
<212> TYPE: PRT
<213> ORGANISM: mus musculus

<400> SEQUENCE: 35

Ser Ile Asn Ser Ala Thr His Tyr Ala Glu Ser Val Lys Gly Arg
 1               5                  10                  15

<210> SEQ ID NO 36
<211> LENGTH: 15
<212> TYPE: PRT
<213> ORGANISM: mus musculus

<400> SEQUENCE: 36

Ser Ala Thr His Tyr Ala Glu Ser Val Lys Gly Arg Phe Thr Ile
 1               5                  10                  15

<210> SEQ ID NO 37
<211> LENGTH: 15
<212> TYPE: PRT
<213> ORGANISM: mus musculus

<400> SEQUENCE: 37

His Tyr Ala Glu Ser Val Lys Gly Arg Phe Thr Ile Ser Arg Asp
 1               5                  10                  15

<210> SEQ ID NO 38
<211> LENGTH: 15
<212> TYPE: PRT
<213> ORGANISM: mus musculus

<400> SEQUENCE: 38

Glu Ser Val Lys Gly Arg Phe Thr Ile Ser Arg Asp Asp Ser Lys
 1               5                  10                  15

<210> SEQ ID NO 39
<211> LENGTH: 15
<212> TYPE: PRT
<213> ORGANISM: mus musculus

<400> SEQUENCE: 39

Lys Gly Arg Phe Thr Ile Ser Arg Asp Asp Ser Lys Ser Ala Val
 1               5                  10                  15

<210> SEQ ID NO 40
<211> LENGTH: 15
<212> TYPE: PRT
<213> ORGANISM: mus musculus
```

-continued

```
<400> SEQUENCE: 40

Phe Thr Ile Ser Arg Asp Asp Ser Lys Ser Ala Val Tyr Leu Gln
1               5                   10                  15

<210> SEQ ID NO 41
<211> LENGTH: 15
<212> TYPE: PRT
<213> ORGANISM: mus musculus

<400> SEQUENCE: 41

Ser Arg Asp Asp Ser Lys Ser Ala Val Tyr Leu Gln Met Thr Asp
1               5                   10                  15

<210> SEQ ID NO 42
<211> LENGTH: 15
<212> TYPE: PRT
<213> ORGANISM: mus musculus

<400> SEQUENCE: 42

Asp Ser Lys Ser Ala Val Tyr Leu Gln Met Thr Asp Leu Arg Thr
1               5                   10                  15

<210> SEQ ID NO 43
<211> LENGTH: 15
<212> TYPE: PRT
<213> ORGANISM: mus musculus

<400> SEQUENCE: 43

Ser Ala Val Tyr Leu Gln Met Thr Asp Leu Arg Thr Glu Asp Thr
1               5                   10                  15

<210> SEQ ID NO 44
<211> LENGTH: 15
<212> TYPE: PRT
<213> ORGANISM: mus musculus

<400> SEQUENCE: 44

Tyr Leu Gln Met Thr Asp Leu Arg Thr Glu Asp Thr Gly Val Tyr
1               5                   10                  15

<210> SEQ ID NO 45
<211> LENGTH: 15
<212> TYPE: PRT
<213> ORGANISM: mus musculus

<400> SEQUENCE: 45

Met Thr Asp Leu Arg Thr Glu Asp Thr Gly Val Tyr Tyr Cys Ser
1               5                   10                  15

<210> SEQ ID NO 46
<211> LENGTH: 15
<212> TYPE: PRT
<213> ORGANISM: mus musculus

<400> SEQUENCE: 46

Leu Arg Thr Glu Asp Thr Gly Val Tyr Tyr Cys Ser Arg Asn Tyr
1               5                   10                  15

<210> SEQ ID NO 47
<211> LENGTH: 15
<212> TYPE: PRT
<213> ORGANISM: mus musculus
```

<400> SEQUENCE: 47

Glu Asp Thr Gly Val Tyr Tyr Cys Ser Arg Asn Tyr Tyr Gly Ser
1               5                   10                  15

<210> SEQ ID NO 48
<211> LENGTH: 15
<212> TYPE: PRT
<213> ORGANISM: mus musculus

<400> SEQUENCE: 48

Gly Val Tyr Tyr Cys Ser Arg Asn Tyr Tyr Gly Ser Thr Tyr Asp
1               5                   10                  15

<210> SEQ ID NO 49
<211> LENGTH: 15
<212> TYPE: PRT
<213> ORGANISM: mus musculus

<400> SEQUENCE: 49

Tyr Cys Ser Arg Asn Tyr Tyr Gly Ser Thr Tyr Asp Tyr Trp Gly
1               5                   10                  15

<210> SEQ ID NO 50
<211> LENGTH: 15
<212> TYPE: PRT
<213> ORGANISM: mus musculus

<400> SEQUENCE: 50

Arg Asn Tyr Tyr Gly Ser Thr Tyr Asp Tyr Trp Gly Gln Gly Thr
1               5                   10                  15

<210> SEQ ID NO 51
<211> LENGTH: 15
<212> TYPE: PRT
<213> ORGANISM: mus musculus

<400> SEQUENCE: 51

Tyr Gly Ser Thr Tyr Asp Tyr Trp Gly Gln Gly Thr Thr Leu Thr
1               5                   10                  15

<210> SEQ ID NO 52
<211> LENGTH: 15
<212> TYPE: PRT
<213> ORGANISM: mus musculus

<400> SEQUENCE: 52

Thr Tyr Asp Tyr Trp Gly Gln Gly Thr Thr Leu Thr Val Ser Ser
1               5                   10                  15

<210> SEQ ID NO 53
<211> LENGTH: 15
<212> TYPE: PRT
<213> ORGANISM: mus musculus

<400> SEQUENCE: 53

Tyr Trp Gly Gln Gly Thr Thr Leu Thr Val Ser Ser Ala Ser Thr
1               5                   10                  15

<210> SEQ ID NO 54
<211> LENGTH: 15
<212> TYPE: PRT
<213> ORGANISM: mus musculus

```
<400> SEQUENCE: 54

Gln Gly Thr Thr Leu Thr Val Ser Ser Ala Ser Thr Lys Gly Pro
  1               5                  10                  15

<210> SEQ ID NO 55
<211> LENGTH: 15
<212> TYPE: PRT
<213> ORGANISM: mus musculus

<400> SEQUENCE: 55

Thr Leu Thr Val Ser Ser Ala Ser Thr Lys Gly Pro Ser Val Phe
  1               5                  10                  15

<210> SEQ ID NO 56
<211> LENGTH: 15
<212> TYPE: PRT
<213> ORGANISM: mus musculus

<400> SEQUENCE: 56

Val Ser Ser Ala Ser Thr Lys Gly Pro Ser Val Phe Pro Leu Ala
  1               5                  10                  15

<210> SEQ ID NO 57
<211> LENGTH: 15
<212> TYPE: PRT
<213> ORGANISM: mus musculus

<400> SEQUENCE: 57

Asp Ile Leu Leu Thr Gln Ser Pro Ala Ile Leu Ser Val Ser Pro
  1               5                  10                  15

<210> SEQ ID NO 58
<211> LENGTH: 15
<212> TYPE: PRT
<213> ORGANISM: mus musculus

<400> SEQUENCE: 58

Leu Thr Gln Ser Pro Ala Ile Leu Ser Val Ser Pro Gly Glu Arg
  1               5                  10                  15

<210> SEQ ID NO 59
<211> LENGTH: 15
<212> TYPE: PRT
<213> ORGANISM: mus musculus

<400> SEQUENCE: 59

Ser Pro Ala Ile Leu Ser Val Ser Pro Gly Glu Arg Val Ser Phe
  1               5                  10                  15

<210> SEQ ID NO 60
<211> LENGTH: 15
<212> TYPE: PRT
<213> ORGANISM: mus musculus

<400> SEQUENCE: 60

Ile Leu Ser Val Ser Pro Gly Glu Arg Val Ser Phe Ser Cys Arg
  1               5                  10                  15

<210> SEQ ID NO 61
<211> LENGTH: 15
<212> TYPE: PRT
<213> ORGANISM: mus musculus
```

```
<400> SEQUENCE: 61

Val Ser Pro Gly Glu Arg Val Ser Phe Ser Cys Arg Ala Ser Gln
1               5                   10                  15

<210> SEQ ID NO 62
<211> LENGTH: 15
<212> TYPE: PRT
<213> ORGANISM: mus musculus

<400> SEQUENCE: 62

Gly Glu Arg Val Ser Phe Ser Cys Arg Ala Ser Gln Phe Val Gly
1               5                   10                  15

<210> SEQ ID NO 63
<211> LENGTH: 15
<212> TYPE: PRT
<213> ORGANISM: mus musculus

<400> SEQUENCE: 63

Val Ser Phe Ser Cys Arg Ala Ser Gln Phe Val Gly Ser Ser Ile
1               5                   10                  15

<210> SEQ ID NO 64
<211> LENGTH: 15
<212> TYPE: PRT
<213> ORGANISM: mus musculus

<400> SEQUENCE: 64

Ser Cys Arg Ala Ser Gln Phe Val Gly Ser Ser Ile His Trp Tyr
1               5                   10                  15

<210> SEQ ID NO 65
<211> LENGTH: 15
<212> TYPE: PRT
<213> ORGANISM: mus musculus

<400> SEQUENCE: 65

Ala Ser Gln Phe Val Gly Ser Ser Ile His Trp Tyr Gln Gln Arg
1               5                   10                  15

<210> SEQ ID NO 66
<211> LENGTH: 15
<212> TYPE: PRT
<213> ORGANISM: mus musculus

<400> SEQUENCE: 66

Phe Val Gly Ser Ser Ile His Trp Tyr Gln Gln Arg Thr Asn Gly
1               5                   10                  15

<210> SEQ ID NO 67
<211> LENGTH: 15
<212> TYPE: PRT
<213> ORGANISM: mus musculus

<400> SEQUENCE: 67

Ser Ser Ile His Trp Tyr Gln Gln Arg Thr Asn Gly Ser Pro Arg
1               5                   10                  15

<210> SEQ ID NO 68
<211> LENGTH: 15
<212> TYPE: PRT
<213> ORGANISM: mus musculus
```

<400> SEQUENCE: 68

His Trp Tyr Gln Gln Arg Thr Asn Gly Ser Pro Arg Leu Leu Ile
1               5                   10                  15

<210> SEQ ID NO 69
<211> LENGTH: 15
<212> TYPE: PRT
<213> ORGANISM: mus musculus

<400> SEQUENCE: 69

Gln Gln Arg Thr Asn Gly Ser Pro Arg Leu Leu Ile Lys Tyr Ala
1               5                   10                  15

<210> SEQ ID NO 70
<211> LENGTH: 15
<212> TYPE: PRT
<213> ORGANISM: mus musculus

<400> SEQUENCE: 70

Thr Asn Gly Ser Pro Arg Leu Leu Ile Lys Tyr Ala Ser Glu Ser
1               5                   10                  15

<210> SEQ ID NO 71
<211> LENGTH: 15
<212> TYPE: PRT
<213> ORGANISM: mus musculus

<400> SEQUENCE: 71

Ser Pro Arg Leu Leu Ile Lys Tyr Ala Ser Glu Ser Met Ser Gly
1               5                   10                  15

<210> SEQ ID NO 72
<211> LENGTH: 15
<212> TYPE: PRT
<213> ORGANISM: mus musculus

<400> SEQUENCE: 72

Leu Leu Ile Lys Tyr Ala Ser Glu Ser Met Ser Gly Ile Pro Ser
1               5                   10                  15

<210> SEQ ID NO 73
<211> LENGTH: 15
<212> TYPE: PRT
<213> ORGANISM: mus musculus

<400> SEQUENCE: 73

Lys Tyr Ala Ser Glu Ser Met Ser Gly Ile Pro Ser Arg Phe Ser
1               5                   10                  15

<210> SEQ ID NO 74
<211> LENGTH: 15
<212> TYPE: PRT
<213> ORGANISM: mus musculus

<400> SEQUENCE: 74

Ser Glu Ser Met Ser Gly Ile Pro Ser Arg Phe Ser Gly Ser Gly
1               5                   10                  15

<210> SEQ ID NO 75
<211> LENGTH: 15
<212> TYPE: PRT
<213> ORGANISM: mus musculus

```
<400> SEQUENCE: 75

Met Ser Gly Ile Pro Ser Arg Phe Ser Gly Ser Gly Ser Gly Thr
 1               5                  10                  15

<210> SEQ ID NO 76
<211> LENGTH: 15
<212> TYPE: PRT
<213> ORGANISM: mus musculus

<400> SEQUENCE: 76

Ile Pro Ser Arg Phe Ser Gly Ser Gly Ser Gly Thr Asp Phe Thr
 1               5                  10                  15

<210> SEQ ID NO 77
<211> LENGTH: 15
<212> TYPE: PRT
<213> ORGANISM: mus musculus

<400> SEQUENCE: 77

Arg Phe Ser Gly Ser Gly Ser Gly Thr Asp Phe Thr Leu Ser Ile
 1               5                  10                  15

<210> SEQ ID NO 78
<211> LENGTH: 15
<212> TYPE: PRT
<213> ORGANISM: mus musculus

<400> SEQUENCE: 78

Gly Ser Gly Ser Gly Thr Asp Phe Thr Leu Ser Ile Asn Thr Val
 1               5                  10                  15

<210> SEQ ID NO 79
<211> LENGTH: 15
<212> TYPE: PRT
<213> ORGANISM: mus musculus

<400> SEQUENCE: 79

Ser Gly Thr Asp Phe Thr Leu Ser Ile Asn Thr Val Glu Ser Glu
 1               5                  10                  15

<210> SEQ ID NO 80
<211> LENGTH: 15
<212> TYPE: PRT
<213> ORGANISM: mus musculus

<400> SEQUENCE: 80

Asp Phe Thr Leu Ser Ile Asn Thr Val Glu Ser Glu Asp Ile Ala
 1               5                  10                  15

<210> SEQ ID NO 81
<211> LENGTH: 15
<212> TYPE: PRT
<213> ORGANISM: mus musculus

<400> SEQUENCE: 81

Leu Ser Ile Asn Thr Val Glu Ser Glu Asp Ile Ala Asp Tyr Tyr
 1               5                  10                  15

<210> SEQ ID NO 82
<211> LENGTH: 15
<212> TYPE: PRT
<213> ORGANISM: mus musculus
```

-continued

```
<400> SEQUENCE: 82

Asn Thr Val Glu Ser Glu Asp Ile Ala Asp Tyr Tyr Cys Gln Gln
1               5                   10                  15

<210> SEQ ID NO 83
<211> LENGTH: 15
<212> TYPE: PRT
<213> ORGANISM: mus musculus

<400> SEQUENCE: 83

Glu Ser Glu Asp Ile Ala Asp Tyr Tyr Cys Gln Gln Ser His Ser
1               5                   10                  15

<210> SEQ ID NO 84
<211> LENGTH: 15
<212> TYPE: PRT
<213> ORGANISM: mus musculus

<400> SEQUENCE: 84

Asp Ile Ala Asp Tyr Tyr Cys Gln Gln Ser His Ser Trp Pro Phe
1               5                   10                  15

<210> SEQ ID NO 85
<211> LENGTH: 15
<212> TYPE: PRT
<213> ORGANISM: mus musculus

<400> SEQUENCE: 85

Asp Tyr Tyr Cys Gln Gln Ser His Ser Trp Pro Phe Thr Phe Gly
1               5                   10                  15

<210> SEQ ID NO 86
<211> LENGTH: 15
<212> TYPE: PRT
<213> ORGANISM: mus musculus

<400> SEQUENCE: 86

Cys Gln Gln Ser His Ser Trp Pro Phe Thr Phe Gly Ser Gly Thr
1               5                   10                  15

<210> SEQ ID NO 87
<211> LENGTH: 15
<212> TYPE: PRT
<213> ORGANISM: mus musculus

<400> SEQUENCE: 87

Ser His Ser Trp Pro Phe Thr Phe Gly Ser Gly Thr Asn Leu Glu
1               5                   10                  15

<210> SEQ ID NO 88
<211> LENGTH: 15
<212> TYPE: PRT
<213> ORGANISM: mus musculus

<400> SEQUENCE: 88

Trp Pro Phe Thr Phe Gly Ser Gly Thr Asn Leu Glu Val Lys Arg
1               5                   10                  15

<210> SEQ ID NO 89
<211> LENGTH: 15
<212> TYPE: PRT
<213> ORGANISM: mus musculus
```

```
<400> SEQUENCE: 89

Thr Phe Gly Ser Gly Thr Asn Leu Glu Val Lys Arg Thr Val Ala
 1               5                  10                  15

<210> SEQ ID NO 90
<211> LENGTH: 15
<212> TYPE: PRT
<213> ORGANISM: mus musculus

<400> SEQUENCE: 90

Ser Gly Thr Asn Leu Glu Val Lys Arg Thr Val Ala Ala Pro Ser
 1               5                  10                  15

<210> SEQ ID NO 91
<211> LENGTH: 15
<212> TYPE: PRT
<213> ORGANISM: mus musculus

<400> SEQUENCE: 91

Asn Leu Glu Val Lys Arg Thr Val Ala Ala Pro Ser Val Phe Ile
 1               5                  10                  15

<210> SEQ ID NO 92
<211> LENGTH: 13
<212> TYPE: PRT
<213> ORGANISM: mus musculus

<400> SEQUENCE: 92

Lys Gly Leu Glu Trp Val Ala Glu Ile Arg Ser Lys Ser
 1               5                  10

<210> SEQ ID NO 93
<211> LENGTH: 13
<212> TYPE: PRT
<213> ORGANISM: mus musculus

<400> SEQUENCE: 93

Glu Trp Val Ala Glu Ile Arg Ser Lys Ser Ile Asn Ser
 1               5                  10

<210> SEQ ID NO 94
<211> LENGTH: 13
<212> TYPE: PRT
<213> ORGANISM: mus musculus

<400> SEQUENCE: 94

Ala Glu Ile Arg Ser Lys Ser Ile Asn Ser Ala Thr His
 1               5                  10

<210> SEQ ID NO 95
<211> LENGTH: 13
<212> TYPE: PRT
<213> ORGANISM: mus musculus

<400> SEQUENCE: 95

Lys Ser Ile Asn Ser Ala Thr His Tyr Ala Glu Ser Val
 1               5                  10

<210> SEQ ID NO 96
<211> LENGTH: 13
<212> TYPE: PRT
<213> ORGANISM: mus musculus
```

```
<400> SEQUENCE: 96

Thr Gly Val Tyr Tyr Cys Ser Arg Asn Tyr Tyr Gly Ser
1               5                   10

<210> SEQ ID NO 97
<211> LENGTH: 13
<212> TYPE: PRT
<213> ORGANISM: mus musculus

<400> SEQUENCE: 97

Ser Thr Tyr Asp Tyr Trp Gly Gln Gly Thr Thr Leu Thr
1               5                   10

<210> SEQ ID NO 98
<211> LENGTH: 13
<212> TYPE: PRT
<213> ORGANISM: mus musculus

<400> SEQUENCE: 98

Ser Gln Phe Val Gly Ser Ser Ile His Trp Tyr Gln Gln
1               5                   10

<210> SEQ ID NO 99
<211> LENGTH: 13
<212> TYPE: PRT
<213> ORGANISM: mus musculus

<400> SEQUENCE: 99

Gln Phe Val Gly Ser Ser Ile His Trp Tyr Gln Gln Arg
1               5                   10

<210> SEQ ID NO 100
<211> LENGTH: 13
<212> TYPE: PRT
<213> ORGANISM: mus musculus

<400> SEQUENCE: 100

Ser Ser Ile His Trp Tyr Gln Gln Arg Thr Asn Gly Ser
1               5                   10

<210> SEQ ID NO 101
<211> LENGTH: 13
<212> TYPE: PRT
<213> ORGANISM: mus musculus

<400> SEQUENCE: 101

His Trp Tyr Gln Gln Arg Thr Asn Gly Ser Pro Arg Leu
1               5                   10

<210> SEQ ID NO 102
<211> LENGTH: 13
<212> TYPE: PRT
<213> ORGANISM: mus musculus

<400> SEQUENCE: 102

Pro Arg Leu Leu Ile Lys Tyr Ala Ser Glu Ser Met Ser
1               5                   10

<210> SEQ ID NO 103
<211> LENGTH: 13
<212> TYPE: PRT
<213> ORGANISM: mus musculus
```

```
<400> SEQUENCE: 103

Arg Leu Leu Ile Lys Tyr Ala Ser Glu Ser Met Ser Gly
  1               5                  10

<210> SEQ ID NO 104
<211> LENGTH: 13
<212> TYPE: PRT
<213> ORGANISM: mus musculus

<400> SEQUENCE: 104

Leu Leu Ile Lys Tyr Ala Ser Glu Ser Met Ser Gly Ile
  1               5                  10

<210> SEQ ID NO 105
<211> LENGTH: 13
<212> TYPE: PRT
<213> ORGANISM: mus musculus

<400> SEQUENCE: 105

Ile Lys Tyr Ala Ser Glu Ser Met Ser Gly Ile Pro Ser
  1               5                  10

<210> SEQ ID NO 106
<211> LENGTH: 13
<212> TYPE: PRT
<213> ORGANISM: mus musculus

<400> SEQUENCE: 106

Glu Ser Met Ser Gly Ile Pro Ser Arg Phe Ser Gly Ser
  1               5                  10

<210> SEQ ID NO 107
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 107
gaagtgaagc tggaggagtc tggaggcggc ttggtgcaac                            40

<210> SEQ ID NO 108
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 108
ctggaggctc catgaaactc tcctgtgttg cctctggatt                            40

<210> SEQ ID NO 109
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 109
cattttcagt aaccactgga tgaactgggt ccgccagtct                            40

<210> SEQ ID NO 110
<211> LENGTH: 40
<212> TYPE: DNA
<213> ORGANISM: Artificial Sequence
```

```
<220> FEATURE:
<223> OTHER INFORMATION: synthetic polynucleotide

<400> SEQUENCE: 110
ccagagaagg ggcttgagtg ggttgctgaa attagatcaa                              40

<210> SEQ ID NO 111
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 111
aatcgattaa ttctgcaaca cattatgcgg agtctgtgaa                              40

<210> SEQ ID NO 112
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 112
agggaggttc accatctcaa gagatgattc caaaagtgct                              40

<210> SEQ ID NO 113
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 113
gtgtacctgc aaatgaccga cctgagaact gaagacactg                              40

<210> SEQ ID NO 114
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 114
gcgtttatta ctgttccagg aattactacg gtagtaccta                              40

<210> SEQ ID NO 115
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 115
cgactactgg ggccaaggca ccactctcac agtgtcctca gg                           42

<210> SEQ ID NO 116
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 116
cctgaggaca ctgtgagagt gg                                                 22
```

<210> SEQ ID NO 117
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 117
tgccttggcc ccagtagtcg taggtactac cgtagtaatt                          40

<210> SEQ ID NO 118
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 118
cctggaacag taataaacgc cagtgtcttc agttctcagg                          40

<210> SEQ ID NO 119
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 119
tcggtcattt gcaggtacac agcactttttg gaatcatctc                         40

<210> SEQ ID NO 120
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 120
ttgagatggt gaacctccct ttcacagact ccgcataatg                          40

<210> SEQ ID NO 121
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 121
tgttgcagaa ttaatcgatt ttgatctaat ttcagcaacc                          40

<210> SEQ ID NO 122
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 122
cactcaagcc ccttctctgg agactggcgg acccagttca                          40

<210> SEQ ID NO 123
<211> LENGTH: 40
<212> TYPE: DNA
<213> ORGANISM: Artificial Sequence
<220> FEATURE:
<223> OTHER INFORMATION: synthetic polynucleotide -continued

<400> SEQUENCE: 123
tccagtggtt actgaaaatg aatccagagg caacacagga                      40

<210> SEQ ID NO 124
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 124
gagtttcatg gagcctccag gttgcaccaa gccgcctcca                      40

<210> SEQ ID NO 125
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 125
gactcctcca gcttcacttc                                            20

<210> SEQ ID NO 126
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 126
agactcctcc agcttcactt cggagtggac acctgtggag ag                   42

<210> SEQ ID NO 127
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 127
accactctca cagtgtcctc aggtgagtcc ttacaacctc tc                   42

<210> SEQ ID NO 128
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 128
ttgggatcct ataaatctct ggcc                                       24

<210> SEQ ID NO 129
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 129
gacatcttgc tgactcagtc tccagccatc ctgtctgtga                      40

<210> SEQ ID NO 130
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 130
gtccaggaga aagagtcagt ttctcctgca gggccagtca                    40

<210> SEQ ID NO 131
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 131
gttcgttggc tcaagcatcc actggtatca gcaaagaaca                    40

<210> SEQ ID NO 132
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 132
aatggttctc caaggcttct cataaagtat gcttctgagt                    40

<210> SEQ ID NO 133
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 133
ctatgtctgg catcccttct agatttagtg gcagtggatc                    40

<210> SEQ ID NO 134
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 134
agggacagat tttactctta gcatcaacac tgtggagtct                    40

<210> SEQ ID NO 135
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 135
gaagatattg cagattatta ctgtcaacaa agtcatagct                    40

<210> SEQ ID NO 136
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 136
ggccattcac gttcggctcg gggacaaatt tggaagtaaa                                40

<210> SEQ ID NO 137
<211> LENGTH: 50
<212> TYPE: DNA
<213> ORGANISM: Artificial Sequence
<220> FEATURE:
<223> OTHER INFORMATION: synthetic polynucleotide

<400> SEQUENCE: 137
acgtgagtag aatttaaact ttgcttcctc agttggatcc tggcagagtc                     50

<210> SEQ ID NO 138
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 138
gactctgcca ggatccaact gaggaagcaa                                           30

<210> SEQ ID NO 139
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 139
agtttaaatt ctactcacgt tttacttcca aatttgtccc                                40

<210> SEQ ID NO 140
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 140
cgagccgaac gtgaatggcc agctatgact ttgttgacag                                40

<210> SEQ ID NO 141
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 141
taataatctg caatatcttc agactccaca gtgttgatgc                                40

<210> SEQ ID NO 142
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 142
taagagtaaa atctgtccct gatccactgc cactaaatct                                40

<210> SEQ ID NO 143
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 143
agaagggatg ccagacatag actcagaagc atactttatg                   40

<210> SEQ ID NO 144
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 144
agaagccttg gagaaccatt tgttctttgc tgataccagt                   40

<210> SEQ ID NO 145
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 145
ggatgcttga gccaacgaac tgactggccc tgcaggagaa                   40

<210> SEQ ID NO 146
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 146
actgactctt tctcctggac tcacagacag gatggctgga                   40

<210> SEQ ID NO 147
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 147
gactgagtca gcaagatgtc                                         20

<210> SEQ ID NO 148
<211> LENGTH: 29
<212> TYPE: DNA
<213> ORGANISM: Artificial Sequence
<220> FEATURE:
<223> OTHER INFORMATION: synthetic polynucleotide

<400> SEQUENCE: 148
ttacgccaag cttatgaata tgcaaatcc                               29

<210> SEQ ID NO 149
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 149
agactgagtc agcaagatgt cggagtggac acctgtggag ag        42

<210> SEQ ID NO 150
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 150
gacatccagc tgactcagtc tccagacacc tcctctgcca        40

<210> SEQ ID NO 151
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 151
ctatgtctgg cgtgccttct agatttagtg gcagtggatc        40

<210> SEQ ID NO 152
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 152
agggacagat tttactctta ccatcaactc cctggaggcc        40

<210> SEQ ID NO 153
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 153
gaagatgccg caacctatta ctgtcaacaa agtcatagct        40

<210> SEQ ID NO 154
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 154
ggccattcac gttcggctcg gggacaaatg tggaagtaaa        40

<210> SEQ ID NO 155
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 155
agtttaaatt ctactcacgt tttacttcca catttgtccc        40

```
<210> SEQ ID NO 156
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 156
taataggttg cggcatcttc ggcctccagg gagttgatgg                    40

<210> SEQ ID NO 157
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 157
agaaggcacg ccagacatag actcagaagc atactttatg                    40

<210> SEQ ID NO 158
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 158
actgactctt tctcctggac tggcagagga ggtgtctgga                    40

<210> SEQ ID NO 159
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 159
gactgagtca gctggatgtc                                          20

<210> SEQ ID NO 160
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 160
agactgagtc agctggatgt cggagtggac acctgtggag ag                 42

<210> SEQ ID NO 161
<211> LENGTH: 80
<212> TYPE: DNA
<213> ORGANISM: Artificial Sequence
<220> FEATURE:
<223> OTHER INFORMATION: synthetic polynucleotide

<400> SEQUENCE: 161
ggatccaact gaggaagcaa agtttaaatt ctactcacgt ttgatttcca cctttgtccc    60
gccgccgaac gtgaatggcc                                          80

<210> SEQ ID NO 162
<211> LENGTH: 33
<212> TYPE: DNA
<213> ORGANISM: Artificial Sequence
```

<220> FEATURE:
<223> OTHER INFORMATION: synthetic polynucleotide

<400> SEQUENCE: 162
agtccaggag aaagagccag tttctcctgc agg      33

<210> SEQ ID NO 163
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 163
cctgcaggag aaactggctc tttctcctgg act      33

<210> SEQ ID NO 164
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 164
ccactggtat cagcacacaa caaatggttc tccaa      35

<210> SEQ ID NO 165
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 165
ttggagaacc atttgttgtg tgctgatacc agtgg      35

<210> SEQ ID NO 166
<211> LENGTH: 62
<212> TYPE: DNA
<213> ORGANISM: Artificial Sequence
<220> FEATURE:
<223> OTHER INFORMATION: synthetic polynucleotide

<400> SEQUENCE: 166
gtctcaggga gcctccaggt tgcaccaagc cgcctccaga ctccaccagc tgcacttcgg      60
ag      62

<210> SEQ ID NO 167
<211> LENGTH: 62
<212> TYPE: DNA
<213> ORGANISM: Artificial Sequence
<220> FEATURE:
<223> OTHER INFORMATION: synthetic polynucleotide

<400> SEQUENCE: 167
aacctggagg ctccctgaga ctctcctgtg ctgcctctgg attcactttc agtaaccact      60
gg      62

<210> SEQ ID NO 168
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 168
aggctgttca tttgcaggta cagagaattt ttggaatcat c     41

<210> SEQ ID NO 169
<211> LENGTH: 50
<212> TYPE: DNA
<213> ORGANISM: Artificial Sequence
<220> FEATURE:
<223> OTHER INFORMATION: synthetic polynucleotide

<400> SEQUENCE: 169
tacctgcaaa tgaacagcct gaaaactgaa gacactgccg tttattactg     50

<210> SEQ ID NO 170
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 170
gaaactagat caaaatcgac taattctgca     30

<210> SEQ ID NO 171
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 171
attagtcgat tttgatctag tttcagcaac     30

<210> SEQ ID NO 172
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 172
cacattatgc ggactctgtg aaaggg     26

<210> SEQ ID NO 173
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 173
ccctttcaca gagtccgcat aatgtg     26

<210> SEQ ID NO 174
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 174
ggccaaggca cccttgtcac agtgtcctca     30

<210> SEQ ID NO 175
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 175
tgaggacact gtgacaaggg tgccttggcc                                30

<210> SEQ ID NO 176
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 176
gccaaggcac cactgtcaca gtgtcctcag g                              31

<210> SEQ ID NO 177
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 177
cctgaggaca ctgtgacagt ggtgccttgg c                              31

<210> SEQ ID NO 178
<211> LENGTH: 13
<212> TYPE: PRT
<213> ORGANISM: Artificial Sequence
<220> FEATURE:
<223> OTHER INFORMATION: synthetic epitope

<400> SEQUENCE: 178

Pro Lys Tyr Val Lys Gln Asn Thr Leu Lys Leu Ala Thr
 1               5                  10

<210> SEQ ID NO 179
<211> LENGTH: 15
<212> TYPE: PRT
<213> ORGANISM: Artificial Sequence
<220> FEATURE:
<223> OTHER INFORMATION: synthetic epitope

<400> SEQUENCE: 179

Lys Val Val Asp Gln Ile Lys Lys Ile Ser Lys Pro Val Gln His
 1               5                  10                  15

<210> SEQ ID NO 180
<211> LENGTH: 13
<212> TYPE: PRT
<213> ORGANISM: mus musculus

<400> SEQUENCE: 180

Val Lys Leu Glu Glu Ser Gly Gly Gly Leu Val Gln Pro
 1               5                  10

<210> SEQ ID NO 181
<211> LENGTH: 13
<212> TYPE: PRT
<213> ORGANISM: mus musculus

```
<400> SEQUENCE: 181

Gly Gly Leu Val Gln Pro Gly Gly Ser Met Lys Leu Ser
 1               5                  10

<210> SEQ ID NO 182
<211> LENGTH: 13
<212> TYPE: PRT
<213> ORGANISM: mus musculus

<400> SEQUENCE: 182

Gly Leu Val Gln Pro Gly Gly Ser Met Lys Leu Ser Cys
 1               5                  10

<210> SEQ ID NO 183
<211> LENGTH: 13
<212> TYPE: PRT
<213> ORGANISM: mus musculus

<400> SEQUENCE: 183

Gly Ser Met Lys Leu Ser Cys Val Ala Ser Gly Phe Ile
 1               5                  10

<210> SEQ ID NO 184
<211> LENGTH: 13
<212> TYPE: PRT
<213> ORGANISM: mus musculus

<400> SEQUENCE: 184

Met Lys Leu Ser Cys Val Ala Ser Gly Phe Ile Phe Ser
 1               5                  10

<210> SEQ ID NO 185
<211> LENGTH: 13
<212> TYPE: PRT
<213> ORGANISM: mus musculus

<400> SEQUENCE: 185

Ser Cys Val Ala Ser Gly Phe Ile Phe Ser Asn His Trp
 1               5                  10

<210> SEQ ID NO 186
<211> LENGTH: 13
<212> TYPE: PRT
<213> ORGANISM: mus musculus

<400> SEQUENCE: 186

Ser Gly Phe Ile Phe Ser Asn His Trp Met Asn Trp Val
 1               5                  10

<210> SEQ ID NO 187
<211> LENGTH: 13
<212> TYPE: PRT
<213> ORGANISM: mus musculus

<400> SEQUENCE: 187

Gly Phe Ile Phe Ser Asn His Trp Met Asn Trp Val Arg
 1               5                  10

<210> SEQ ID NO 188
<211> LENGTH: 13
<212> TYPE: PRT
<213> ORGANISM: mus musculus
```

```
<400> SEQUENCE: 188

Phe Ile Phe Ser Asn His Trp Met Asn Trp Val Arg Gln
1               5                   10

<210> SEQ ID NO 189
<211> LENGTH: 13
<212> TYPE: PRT
<213> ORGANISM: mus musculus

<400> SEQUENCE: 189

Asn His Trp Met Asn Trp Val Arg Gln Ser Pro Glu Lys
1               5                   10

<210> SEQ ID NO 190
<211> LENGTH: 13
<212> TYPE: PRT
<213> ORGANISM: mus musculus

<400> SEQUENCE: 190

His Trp Met Asn Trp Val Arg Gln Ser Pro Glu Lys Gly
1               5                   10

<210> SEQ ID NO 191
<211> LENGTH: 13
<212> TYPE: PRT
<213> ORGANISM: mus musculus

<400> SEQUENCE: 191

Met Asn Trp Val Arg Gln Ser Pro Glu Lys Gly Leu Glu
1               5                   10

<210> SEQ ID NO 192
<211> LENGTH: 13
<212> TYPE: PRT
<213> ORGANISM: mus musculus

<400> SEQUENCE: 192

Asn Trp Val Arg Gln Ser Pro Glu Lys Gly Leu Glu Trp
1               5                   10

<210> SEQ ID NO 193
<211> LENGTH: 13
<212> TYPE: PRT
<213> ORGANISM: mus musculus

<400> SEQUENCE: 193

Leu Glu Trp Val Ala Glu Ile Arg Ser Lys Ser Ile Asn
1               5                   10

<210> SEQ ID NO 194
<211> LENGTH: 13
<212> TYPE: PRT
<213> ORGANISM: mus musculus

<400> SEQUENCE: 194

Thr His Tyr Ala Glu Ser Val Lys Gly Arg Phe Thr Ile
1               5                   10

<210> SEQ ID NO 195
<211> LENGTH: 13
<212> TYPE: PRT
<213> ORGANISM: mus musculus
```

-continued

```
<400> SEQUENCE: 195

Glu Ser Val Lys Gly Arg Phe Thr Ile Ser Arg Asp Asp
1               5                   10

<210> SEQ ID NO 196
<211> LENGTH: 13
<212> TYPE: PRT
<213> ORGANISM: mus musculus

<400> SEQUENCE: 196

Gly Arg Phe Thr Ile Ser Arg Asp Asp Ser Lys Ser Ala
1               5                   10

<210> SEQ ID NO 197
<211> LENGTH: 13
<212> TYPE: PRT
<213> ORGANISM: mus musculus

<400> SEQUENCE: 197

Phe Thr Ile Ser Arg Asp Asp Ser Lys Ser Ala Val Tyr
1               5                   10

<210> SEQ ID NO 198
<211> LENGTH: 13
<212> TYPE: PRT
<213> ORGANISM: mus musculus

<400> SEQUENCE: 198

Ser Ala Val Tyr Leu Gln Met Thr Asp Leu Arg Thr Glu
1               5                   10

<210> SEQ ID NO 199
<211> LENGTH: 13
<212> TYPE: PRT
<213> ORGANISM: mus musculus

<400> SEQUENCE: 199

Ala Val Tyr Leu Gln Met Thr Asp Leu Arg Thr Glu Asp
1               5                   10

<210> SEQ ID NO 200
<211> LENGTH: 13
<212> TYPE: PRT
<213> ORGANISM: mus musculus

<400> SEQUENCE: 200

Val Tyr Leu Gln Met Thr Asp Leu Arg Thr Glu Asp Thr
1               5                   10

<210> SEQ ID NO 201
<211> LENGTH: 13
<212> TYPE: PRT
<213> ORGANISM: mus musculus

<400> SEQUENCE: 201

Leu Gln Met Thr Asp Leu Arg Thr Glu Asp Thr Gly Val
1               5                   10

<210> SEQ ID NO 202
<211> LENGTH: 13
<212> TYPE: PRT
<213> ORGANISM: mus musculus
```

```
<400> SEQUENCE: 202

Thr Asp Leu Arg Thr Glu Asp Thr Gly Val Tyr Tyr Cys
 1               5                  10

<210> SEQ ID NO 203
<211> LENGTH: 13
<212> TYPE: PRT
<213> ORGANISM: mus musculus

<400> SEQUENCE: 203

Gly Val Tyr Tyr Cys Ser Arg Asn Tyr Tyr Gly Ser Thr
 1               5                  10

<210> SEQ ID NO 204
<211> LENGTH: 13
<212> TYPE: PRT
<213> ORGANISM: mus musculus

<400> SEQUENCE: 204

Val Tyr Tyr Cys Ser Arg Asn Tyr Tyr Gly Ser Thr Tyr
 1               5                  10

<210> SEQ ID NO 205
<211> LENGTH: 13
<212> TYPE: PRT
<213> ORGANISM: mus musculus

<400> SEQUENCE: 205

Arg Asn Tyr Tyr Gly Ser Thr Tyr Asp Tyr Trp Gly Gln
 1               5                  10

<210> SEQ ID NO 206
<211> LENGTH: 13
<212> TYPE: PRT
<213> ORGANISM: mus musculus

<400> SEQUENCE: 206

Asn Tyr Tyr Gly Ser Thr Tyr Asp Tyr Trp Gly Gln Gly
 1               5                  10

<210> SEQ ID NO 207
<211> LENGTH: 13
<212> TYPE: PRT
<213> ORGANISM: mus musculus

<400> SEQUENCE: 207

Tyr Asp Tyr Trp Gly Gln Gly Thr Thr Leu Thr Val Ser
 1               5                  10

<210> SEQ ID NO 208
<211> LENGTH: 13
<212> TYPE: PRT
<213> ORGANISM: mus musculus

<400> SEQUENCE: 208

Asp Ile Leu Leu Thr Gln Ser Pro Ala Ile Leu Ser Val
 1               5                  10

<210> SEQ ID NO 209
<211> LENGTH: 13
<212> TYPE: PRT
<213> ORGANISM: mus musculus
```

-continued

<400> SEQUENCE: 209

Ile Leu Leu Thr Gln Ser Pro Ala Ile Leu Ser Val Ser
1               5                   10

<210> SEQ ID NO 210
<211> LENGTH: 13
<212> TYPE: PRT
<213> ORGANISM: mus musculus

<400> SEQUENCE: 210

Pro Ala Ile Leu Ser Val Ser Pro Gly Glu Arg Val Ser
1               5                   10

<210> SEQ ID NO 211
<211> LENGTH: 13
<212> TYPE: PRT
<213> ORGANISM: mus musculus

<400> SEQUENCE: 211

Ala Ile Leu Ser Val Ser Pro Gly Glu Arg Val Ser Phe
1               5                   10

<210> SEQ ID NO 212
<211> LENGTH: 13
<212> TYPE: PRT
<213> ORGANISM: mus musculus

<400> SEQUENCE: 212

Leu Ser Val Ser Pro Gly Glu Arg Val Ser Phe Ser Cys
1               5                   10

<210> SEQ ID NO 213
<211> LENGTH: 13
<212> TYPE: PRT
<213> ORGANISM: mus musculus

<400> SEQUENCE: 213

Glu Arg Val Ser Phe Ser Cys Arg Ala Ser Gln Phe Val
1               5                   10

<210> SEQ ID NO 214
<211> LENGTH: 13
<212> TYPE: PRT
<213> ORGANISM: mus musculus

<400> SEQUENCE: 214

Val Ser Phe Ser Cys Arg Ala Ser Gln Phe Val Gly Ser
1               5                   10

<210> SEQ ID NO 215
<211> LENGTH: 13
<212> TYPE: PRT
<213> ORGANISM: mus musculus

<400> SEQUENCE: 215

Ile His Trp Tyr Gln Gln Arg Thr Asn Gly Ser Pro Arg
1               5                   10

<210> SEQ ID NO 216
<211> LENGTH: 13
<212> TYPE: PRT
<213> ORGANISM: mus musculus

```
<400> SEQUENCE: 216

Ser Gly Ile Pro Ser Arg Phe Ser Gly Ser Gly Ser Gly
1               5                   10

<210> SEQ ID NO 217
<211> LENGTH: 13
<212> TYPE: PRT
<213> ORGANISM: mus musculus

<400> SEQUENCE: 217

Ser Arg Phe Ser Gly Ser Gly Ser Gly Thr Asp Phe Thr
1               5                   10

<210> SEQ ID NO 218
<211> LENGTH: 13
<212> TYPE: PRT
<213> ORGANISM: mus musculus

<400> SEQUENCE: 218

Thr Asp Phe Thr Leu Ser Ile Asn Thr Val Glu Ser Glu
1               5                   10

<210> SEQ ID NO 219
<211> LENGTH: 13
<212> TYPE: PRT
<213> ORGANISM: mus musculus

<400> SEQUENCE: 219

Phe Thr Leu Ser Ile Asn Thr Val Glu Ser Glu Asp Ile
1               5                   10

<210> SEQ ID NO 220
<211> LENGTH: 13
<212> TYPE: PRT
<213> ORGANISM: mus musculus

<400> SEQUENCE: 220

Leu Ser Ile Asn Thr Val Glu Ser Glu Asp Ile Ala Asp
1               5                   10

<210> SEQ ID NO 221
<211> LENGTH: 13
<212> TYPE: PRT
<213> ORGANISM: mus musculus

<400> SEQUENCE: 221

Asn Thr Val Glu Ser Glu Asp Ile Ala Asp Tyr Tyr Cys
1               5                   10

<210> SEQ ID NO 222
<211> LENGTH: 13
<212> TYPE: PRT
<213> ORGANISM: mus musculus

<400> SEQUENCE: 222

Glu Asp Ile Ala Asp Tyr Tyr Cys Gln Gln Ser His Ser
1               5                   10

<210> SEQ ID NO 223
<211> LENGTH: 13
<212> TYPE: PRT
<213> ORGANISM: mus musculus
```

```
-continued

<400> SEQUENCE: 223

Ala Asp Tyr Tyr Cys Gln Gln Ser His Ser Trp Pro Phe
1               5                   10

<210> SEQ ID NO 224
<211> LENGTH: 13
<212> TYPE: PRT
<213> ORGANISM: mus musculus

<400> SEQUENCE: 224

Asp Tyr Tyr Cys Gln Gln Ser His Ser Trp Pro Phe Thr
1               5                   10

<210> SEQ ID NO 225
<211> LENGTH: 13
<212> TYPE: PRT
<213> ORGANISM: mus musculus

<400> SEQUENCE: 225

His Ser Trp Pro Phe Thr Phe Gly Ser Gly Thr Asn Leu
1               5                   10

<210> SEQ ID NO 226
<211> LENGTH: 13
<212> TYPE: PRT
<213> ORGANISM: mus musculus

<400> SEQUENCE: 226

Trp Pro Phe Thr Phe Gly Ser Gly Thr Asn Leu Glu Val
1               5                   10
```

MODIFIED ANTI-TNF ALPHA ANTIBODY

This application is the National Stage of International Application Ser. No. PCT/EP02/12566 filed on Nov. 11, 2002.

FIELD OF THE INVENTION

The present invention relates to polypeptides to be administered especially to humans and in particular for therapeutic use. The polypeptides are modified polypeptides whereby the modification results in a reduced propensity for the polypeptide to elicit an immune response upon administration to the human subject. The invention in particular relates to the modification of antibodies reactive to human tumor necrosis factor alpha (TNF alpha) to result in anti-TNF alpha antibodies that are substantially non-immunogenic or less immunogenic than any non-modified counterpart when used in vivo.

BACKGROUND OF THE INVENTION

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response [Schroff, R. W. et al (1985) Cancer Res. 45: 879-885; Shawler, D. L. et al (1985) J. Immunol. 135: 1530-1535]. For monoclonal antibodies, a number of techniques have been developed in attempt to reduce the HAMA response [WOA8909622; EPA0239400; EPA0438310; WOA9106667; EPA0699755]. These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients [Issacs J. D. (1990) Sem. Immunol. 2: 449, 456; Rebello, P. R. et al (1999) Transplantation 68: 1417-1420].

Antibodies are not the only class of polypeptide molecule administered as a therapeutic agent against which an immune response may be mounted. Even proteins of human origin and with the same amino acid sequences as occur within humans can still induce an immune response in humans. Notable examples include therapeutic use of granulocyte-macrophage colony stimulating factor [Wadhwa, M. et al (1999) Clin. Cancer Res. 5: 1353-1361] and interferon alpha 2 [Russo, D. et al (1996) Bri. J. Haem. 94: 300-305; Stein, R. et al (1988) New Engl. J. Med. 318: 1409-1413] amongst others.

Key to the induction of an immune response is the presence within the protein of peptides that can stimulate the activity of T-cells via presentation on MHC class II molecules, so-called "T-cell epitopes". Such T-cell epitopes are commonly defined as any amino acid residue sequence with the ability to bind to MHC Class II molecules. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response.

MHC Class II molecules are a group of highly polymorphic proteins which play a central role in helper T-cell selection and activation. The human leukocyte antigen group DR (HLA-DR) are the predominant isotype of this group of proteins however, isotypes HLA-DQ and HLA-DP perform similar functions. The present invention is applicable to the detection of T-cell epitopes presented within the context of DR, DP or DQ MHC Class II. In the human population, individuals bear two to four DR alleles, two DQ and two DP alleles. The structure of a number of DR molecules has been solved and these appear as an open-ended peptide binding groove with a number of hydrophobic pockets which engage hydrophobic residues (pocket residues) of the peptide [Brown et al Nature (1993) 364: 33: Stem et al (1994) Nature 368: 215]. Polymorphism identifying the different allotypes of class II molecule contributes to a wide diversity of different binding surfaces for peptides within the peptide binding grove and at the population level ensures maximal flexibility with regard to the ability to recognize foreign proteins and mount an immune response to pathogenic organisms.

An immune response to a therapeutic protein proceeds via the MHC class II peptide presentation pathway. Here exogenous proteins are engulfed and processed for presentation in association with MHC class II molecules of the DR, DQ or DP type. MHC Class II molecules are expressed by professional antigen presenting cells (APCs), such as macrophages and dendritic cells amongst others. Engagement of a MHC class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response.

T-cell epitope identification is the first step to epitope elimination, however there are few clear cases in the art where epitope identification and epitope removal are integrated into a single scheme. Thus WO98/52976 and WO00/34317 teach computational threading approaches to identifying polypeptide sequences with the potential to bind a sub-set of human MHC class II DR allotypes. In these teachings, predicted T-cell epitopes are removed by the use of judicious amino acid substitution within the protein of interest. However with this scheme and other computationally based procedures for epitope identification [Godkin, A. J. et al (1998) J. Immunol. 161: 850-858; Sturniolo, T. et al (1999) Nat. Biotechnol. 17: 555-561], peptides predicted to be able to bind MHC class II molecules may not function as T-cell epitopes in all situations, particularly, in vivo due to the processing pathways or other phenomena. In addition, the computational approaches to T-cell epitope prediction have in general not been capable of predicting epitopes with DP or DQ restriction.

Besides computational techniques, there are in vitro methods for measuring the ability of synthetic peptides to bind MHC class II molecules. An exemplary method uses B-cell lines of defined MHC allotype as a source of MHC class II binding surface and may be applied to MHC class II ligand identification [Marshall K. W. et al. (1994) J. Immunol. 152: 4946-4956; O'Sullivan et al (1990) J. Immunol. 145: 1799-1808; Robadey C. et al (1997) J. Immunol 159: 3238-3246]. However, such techniques are not adapted for the screening multiple potential epitopes to a wide diversity of MHC allotypes, nor can they confirm the ability of a binding peptide to function as a T-cell epitope.

Recently techniques exploiting soluble complexes of recombinant MHC molecules in combination with synthetic peptides have come into use [Kern, F. et al (1998) Nature Medicine 4:975-978; Kwok, W. W. et al (2001) TRENDS in Immunol. 22:583-588]. These reagents and procedures are used to identify the presence of T-cell clones from peripheral blood samples from human or experimental animal subjects that are able to bind particular MHC-peptide complexes and are not adapted for the screening multiple potential epitopes to a wide diversity of MHC allotypes.

Biological assays of T-cell activation can provide a practical option to providing a reading of the ability of a test peptide/protein sequence to evoke an immune response. Examples of this kind of approach include the work of Petra et al using T-cell proliferation assays to the bacterial protein staphylokinase, followed by epitope mapping using synthetic peptides to stimulate T-cell lines [Petra, A. M. et al (2002) *J. Immunol.* 168: 155-161]. Similarly, T-cell proliferation assays using synthetic peptides of the tetanus toxin protein have resulted in definition of immunodominant epitope regions of the toxin [Reece J. C. et al (1993) *J. Immunol.* 151: 6175-6184]. WO99/53038 discloses an approach whereby T-cell epitopes in a test protein may be determined using isolated sub-sets of human immune cells, promoting their differentiation in vitro and culture of the cells in the presence of synthetic peptides of interest and measurement of any induced proliferation in the cultured T-cells. The same technique is also described by Stickler et al [Stickler, M. M. et al (2000) *J. Immunotherapy* 23:654-660], where in both instances the method is applied to the detection of T-cell epitopes within bacterial subtilisin. Such a technique requires careful application of cell isolation techniques and cell culture with multiple cytokine supplements to obtain the desired immune cell sub-sets (dendritic cells, CD4+ and or CD8+T-cells) and is not conducive to rapid through-put screening using multiple donor samples.

As depicted above and as consequence thereof, it would be desirable to identify and to remove or at least to reduce T-cell epitopes from a given in principal therapeutically valuable but originally immunogenic peptide, polypeptide or protein. One of these therapeutically valuable molecules is a monoclonal antibody with binding specificity for tumor necrosis factor alpha (TNF alpha). The preferred monoclonal antibody of the present invention is a modified form of the antibody cA2 described in U.S. Pat. No. 6,284,471. The antibody cA2 is herein referred to as the "parental" antibody of the invention.

It is an objective of the invention to provide for modified forms of the parental mouse-derived monoclonal antibody with binding specificity to human TNF alpha with one or more T cell epitopes removed. TNF alpha is involved in the mediation of a number of pathological conditions including Crohn's disease, rheumatoid arthritis and endotoxic or cardiovascular shock. The modified antibody of the invention can be expected to have therapeutic utility in these conditions and other diseases in which TNF alpha is a significant component of the pathophysiology.

The cA2 antibody is not the only antibody with binding specificity for TNF alpha. A variety of polyclonal and monoclonal preparations with similar specificity are known in the art. Examples include the anti-TNF alpha preparations disclosed in EP0212489, EP0218868, EP0288088 and WO91/02078. Further examples of rodent or murine monoclonal antibodies specific for recombinant human TNF alpha have been described in the literature [see for example; Liang, et al (1986) *Biochem. Biophys. Res. Comm.* 137: 847-854; Meager, et al. (1987), *Hybridoma* 6: 305-311; Fendly et al. (1987), *Hybridoma* 6: 359-369; Bringman, et al (1987), *Hybridoma* 6: 489-507; Hirai, et al., (1987) *J. Immunol. Meth.* 96: 57-62 and Moller, et al (1990), *Cytokine* 2: 162-169]. Some of these antibodies are able to neutralise the effect of TNF alpha in vitro and have been used to develop immunoassays for TNF alpha or are used in the purification of recombinant TNF alpha. In general, and in contrast with antibody cA2, these antibodies have not been developed for in vivo diagnostic or therapeutic uses in humans.

Clinical studies have however been conducted using a murine anti-TNF alpha antibody in human subjects. In fourteen patients with severe septic shock receiving a single dose of a murine anti-TNF alpha antibody seven developed a human anti-murine antibody response to the treatment, due to the immunogenicity of the therapeutic murine antibody. [Exley, A. R. et al.(1990), *Lancet* 335: 1275-1277]. Such immunogenicity can render treatment ineffective in patients undergoing diagnostic or therapeutic administration of murine anti-TNF alpha antibodies.

In this regard, Adair et al [EP0927758] describe recombinant antibody molecules including antibodies with human constant region sequences and versions in which the complementarity determining regions (CDRs) have been engrafted onto modified human antibody framework sequences. Such antibodies and humanized antibodies are claimed to retain specificity to human TNF alpha□ and may be used in diagnosis and therapy.

The clinical use of antibody cA2 is described by Le et al [U.S. Pat. No. 5,919,425] who detail methods of treating TNF alpha mediated disease using cA2 which is in fact a chimeric form of an original murine monoclonal antibody designated A2. Similarly, Feldmen et al [U.S. Pat. No. 6,270,766] describe use of the same antibody in combination therapy with a myeloablative agent methotrexate for the treatment of arthritis and Crohn's disease.

Large clinical trials have now been conducted using this antibody, which has received the compound name "infliximab", and is traded in some territories as REMICADE. This antibody has demonstrated a degree of therapeutic efficacy in the treatment of rheumatoid arthritis and Crohn's disease has received regulatory approval for its use as in Crohn's disease in the USA and in Europe. The antibody is produced by recombinant techniques and as noted above, the antibody is "chimeric" meaning that the constant region of the antibody is comprised of sequence derived from human constant region genes and the contribution of mouse derived protein sequence is therefore reduced. Despite this up to 13% of patients treated for Crohn's disease showed an immune response to the therapeutic antibody [Mani R. N. et al. (1998) *Arthritis Rheum.* 41:1552-1563; Elliot M. J. et al (1994) *Lancet* 344: 1105-1110; Targan S. R. et al (1997) *N. Engl. J. Med.* 337: 1029-1035; Present D. H. et al (1999) *N. Engl. J. Med.* 340: 1398-1405].

There is therefore a need for anti-TNF alpha antibody analogues with enhanced properties and especially improvements in the biological properties of the protein. In this regard, it is highly desired to provide anti-TNF alpha antibodies with reduced or absent potential to induce an immune response in the human subject. Such proteins would expect to display an increased circulation time within the human subject and would be of particular benefit in chronic or recurring disease settings such as is the case for a number of indications for anti-TNF alpha antibodies. The present invention provides for modified forms of an anti-TNF alpha antibody that are expected to display enhanced properties in vivo.

It is a particular objective of the present invention to provide modified anti-TNF alpha antibodies in which the immune characteristic is modified by means of reduced numbers of potential T-cell epitopes.

The invention discloses sequences identified within the variable region sequences of the heavy and light chains of an anti-TNF alpha antibody that are potential T cell epitopes by virtue of MHC class II binding potential.

The invention further discloses sequences identified within the variable region sequences of the heavy and light chains of an anti-TNF alpha antibody that are potential T cell epitopes by virtue of their ability when presented as synthetic peptides to a population of human peripheral blood mononuclear cells (PBMC) cultured in vitro to induce a proliferative response in said PBMC cells. Such information thereby has enabled the constitution of a map of T-cell epitopes present in the said variable regions of the antibody and has provided the critical information required for removing the T-cell epitopes from the molecule.

Where others have provided anti-TNF alpha antibody molecules including chimeric [U.S. Pat. No. 5,919,425] and humanized [EP0927758] forms, none of these teachings recognize the importance of T cell epitopes to the immunogenic properties of the protein nor have been conceived to directly influence said properties in a specific and controlled way according to the scheme of the present invention.

SUMMARY AND DESCRIPTION OF THE INVENTION

The present invention provides for a modified antibody in which the immune characteristic is modified by means of reduced or removed numbers of potential T-cell epitopes.

The preferred murine derived non-modified "parental" monoclonal antibody of the present invention is herein referred to as antibody cA2 is described in U.S. Pat. No. 6,284,471.

The present invention discloses sequences identified within the cA2 variable region sequences of both the heavy chain and light chain that are potential T-cell epitopes by virtue of MHC class II binding potential.

The invention further discloses the major regions of the antibody V-region sequence that are immunogenic in man and thereby provides the critical information required to conduct modification to the sequences to eliminate or reduce the immunogenic effectiveness of these sites.

In one aspect, the invention provides a modified antibody molecule having specificity for an antigen recognized by monoclonal antibody cA2 wherein one or more amino acids in the variable region of the said cA2 antibody is substituted to reduce MHC class II recognition of peptides derived from this region.

In another aspect, the invention provides a variant monoclonal antibody with reduced immunogenic potential in humans, said variant comprising one or more amino acid substitutions in the V-region of the cA2 antibody to eliminate or reduce peptide fragments of the said V-region from acting as MHC class II ligands or being able to stimulate T-cells.

In a further aspect of the invention, there is provided a variant monoclonal antibody with reduced immunogenic potential in humans, said variant comprising a combination of heavy and light chain V-regions comprising the amino acid sequences selected from Vh1/Vk1, Vh1/Vk5, Vh1/Vk8, Vh5/Vk12, Vh8/Vk5.

It is most preferred to provide and antibody featuring the combination of V-region domains Vh5/Vk12 although other combinations of V-region compositions as listed above may be contemplated.

The sequences of the above listed Vh and Vk sequences are detailed in full in the itemized summary below and as FIG. 8 which also sets out the SEQ ID No assignments as used herein.

Accordingly, the present invention provides modified anti-TNF alpha antibodies with reduced immunogenicity in man where the modified antibodies comprise heavy and light chain variable region amino acid sequences selected from SEQ ID No:1/SEQ ID No:5, SEQ ID No:1/SEQ ID No:7, SEQ ID No: 1/SEQ ID No:8, SEQ ID No:3/SEQ ID No:6 and SEQ ID No:4/SEQ ID No:7 or combinations of amino acids having at least 70% similarity to one or both amino acid sequences in each of the above listed pairs.

The sequences according to this invention designated as SEQ ID 1-8 are:

```
SEQ ID No: 1 (= Vh 1)
EVQLVESGGGLVQPGGSLRLSCAASGFTFSNHWMNWVRQSPEKGLEWVAE

IRSKSINSATHYAESVKGRFTISRDDSKNSLYLQNNSLKTEDTAVYYCSR

NYYGSTYDYWGQGTTLTVSS

SEQ ID No: 2 (= Vh 3)
EVKLEESGGGLVQPGGSLRLSCAASGFTFSNHWMNWVRQSPEKGLEWVAE

IRSKSINSATHYAESVKGRFTISRDDSKNSLYLQMNSLKTEDTGVYYCSR

NYYGSTYDYWGQGTTVTVSS

SEQ ID No: 3 (= Vh 5)
EVKLEESGGGLVQPGGSLRLSCAASGFTFSNHWMNWVRQSPEKGLEWVAE

TRSKSTNSATHYAESVKGRFTISRDDSKNSLYLQMNSLKTEDTGVYYCSR

NYYGSTYDYWGQGTTVTVSS

SEQ ID No: 4 (= Vh 8)
EVQLVESGGGLVQPGGSLRLSCAASGFTFSNHWMNWVRQSPEKGLEWVAE

TRSKSTNSATHYADSVKGRFTISRDDSKNSLYLQMNSLKTEDTAVYYCSR

NYYGSTYDYWGQGTLVTVSS

SEQ ID No: 5 (= Vk 1)
DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGS

GTNVEVKR

SEQ ID No: 6 (= Vk 12)
DIQLTQSPDTSSASPGERASFSCRASQFVGSSIHWYQHTTNGSPRLLIKY

ASESMSGVPSRFSGSGSGTDFTLTINSLEAEDAATYYCQQSHSWPFTFGS

GTNLEVKR

SEQ ID No: 7 (= Vk 5)
DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGG

GTKVEIKR

SEQ ID No: 8 (= Vk 8)
DIQLTQSPDTSSASPGERASFSCRASQFVGVVIHWYQHTTNGSPRLLIKY

ASESMSGVPSRFSGSGSGTDFTLTINSLEAEDAATYYCQQSHSWPFTFGG

GTKVEIKR
```

In summary the invention relates to the following issues:
a monoclonal antibody V-region heavy chain termed herein Vh1, comprising, in single letter code, the amino acid sequence (SEQ ID NO: 1)
EVQLVESGGGLVQPGGSLRLSCAASGFTFSNHWMN-WVRQSPEKGLEWVAEIRSKSINSATHYAESVKGRF-TISRDDSKNSLYLQMNSLKTEDTAVYYCSRNYYGS-TYDYWGQGTTLTVSS;
a monoclonal antibody V-region heavy chain termed herein Vh3, comprising, in single letter code, the amino acid sequence (SEQ ID NO: 2)
EVKLEESGGGLVQPGGSLRLSCAASGFTFSNHWMN-WVRQSPEKGLEWVAEIRSKSINSATHYAESVKGRF-TISRDDSKNSLYLQMNSLKTEDTGVYYCSRNYYG-STYDYWGQGTTVTVSS;

a monoclonal antibody V-region heavy chain termed herein Vh5 comprising, in single letter code, the amino acid sequence (SEQ ID NO: 3)

EVKLEESGGGLVQPGGSLRLSCAASGFTFSNHWMN-WVRQSPEKGLEWVAETRSKSTNSATHYAESVKG-RFTISRDDSKNSLYLQMNSLKTEDTGVYYCSRNY-YGSTYDYWGQGTTVTVSS;

a monoclonal antibody V-region heavy chain termed herein Vh8, comprising, in single letter code, the amino acid sequence (SEQ ID NO: 4)

EVQLVESGGGLVQPGGSLRLSCAASGFTFSNHWMNWVRQSPEKGLEWVAE

TRSKSTNSATHYADSVKGRFTISRDDSKNSLYLQMNSLKTEDTAVYYCSR

NYYGSTYDYWGQGTLVTVSS;

a monoclonal antibody V-region light chain termed herein Vk1, comprising, in single letter code, the amino acid sequence (SEQ ID NO: 5)

DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGS

GTNVEVKR;

a monoclonal antibody V-region light chain termed herein Vk12, comprising, in single letter code, the amino acid sequence (SEQ ID NO: 6)

DIQLTQSPDTSSASPGERASFSCRASQFVGSSIHWYQHTTNGSPRLLIKY

ASESMSGVPSRFSGSGSGTDFTLTINSLEAEDAATYYCQQSHSWPFTFGS

GTNLEVKR;

a monoclonal antibody V-region light chain termed herein Vk5, comprising, in single letter code, the amino acid sequence (SEQ ID NO: 7)

DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGG

GTKVEIKR;

a monoclonal antibody V-region light chain termed herein Vk8, comprising, in single letter code, the amino acid sequence (SEQ ID NO: 8)

DIQLTQSPDTSSASPGERASFSCRASQFVGSSIHWYQHTTNGSPRLLIKY

ASESMSGVPSRFSGSGSGTDFTLTINSLEAEDAATYYCQQSHSWPFTFGG

GTKVEIKR;

a monoclonal antibody comprising the heavy chain V-region sequence Vh1 and a the light chain sequence Vk1
a monoclonal antibody comprising the heavy chain V-region sequence Vh1 and a the light chain sequence Vk5
a monoclonal antibody comprising the heavy chain V-region sequence Vh1 and a the light chain sequence Vk8
a monoclonal antibody comprising the heavy chain V-region sequence Vh5 and a the light chain sequence Vk12
a monoclonal antibody comprising the heavy chain V-region sequence Vh8 and a the light chain sequence Vk5
a monoclonal antibody V-region heavy chain comprising the amino acid sequence of antibody cA2 modified to contain one or more substitutions selected from the group of substitutions; M18L, K19R, V23A, I28T, I51T, I56T, S79N, A80S, V81L, T86N, D87S, R89K, L116V wherein the amino acids are identified using single letter code and the numbering refers to the numerical position of the amino acid where the N-terminal residue equals residue 1;

a monoclonal antibody V-region heavy chain comprising the amino acid sequence of antibody cA2 modified to contain one or more substitutions selected from the group of substitutions K3Q, E5V, M18L, K19R, V23A, I28T, S79N, A80S, V81L, T86N, D87S, R89K, G94A wherein the amino acids are identified using single letter code and the numbering refers to the numerical position of the amino acid where the N-terminal residue equals residue 1;

a monoclonal antibody V-region heavy chain comprising the amino acid sequence of antibody cA2 modified to contain one or more substitutions selected from the group of substitutions M18L, K19R, V23A, I28T, S79N, A80S, V81L, T86N, D87S, R89K, L116V wherein the amino acids are identified using single letter code and the numbering refers to the numerical position of the amino acid where the N-terminal residue equals residue 1;

a monoclonal antibody V-region heavy chain comprising the amino acid sequence of antibody cA2 modified to contain one or more substitutions selected from the group of substitutions K3Q, E5V, M18L, K19R, V23A, I28T, I51T, I56T, E64D, S79N, A80S, V81L, T86N, D87S, R89K, G94A, T115L, L116V wherein the amino acids are identified using single letter code and the numbering refers to the numerical position of the amino acid where the N-terminal residue equals residue 1;

a monoclonal antibody V-region light chain comprising the amino acid sequence of antibody cA2 modified to contain one or more substitutions selected from the group of substitutions; L3Q, A9D, I10T, L11S, V13A, V19A, Q38H, R39T, I58V, S74T, T77S, V78L, S80A, I83A, D85T wherein the amino acids are identified using single letter code and the numbering refers to the numerical position of the amino acid where the N-terminal residue equals residue 1;

a monoclonal antibody V-region light chain comprising the amino acid sequence of antibody cA2 modified to contain one or more substitutions selected from the group of substitutions L3Q, A9D, I10T, L11S, V13A, I58V, S74T, T77S, V78L, S80A, I83A, D85T, L104V wherein the amino acids are identified using single letter code and the numbering refers to the numerical position of the amino acid where the N-terminal residue equals residue 1;

a monoclonal antibody V-region light chain comprising the amino acid sequence of antibody cA2 modified to contain one or more substitutions selected from the group of substitutions L3Q, A9D, I10T, L11S, V13A, I58V, S74T, T77S, V78L, S80A, I83A, D85T, S100G, N103K, L104V, V106I wherein the amino acids are identified using single letter code and the numbering refers to the numerical position of the amino acid where the N-terminal residue equals residue 1;

a monoclonal antibody V-region light chain comprising the amino acid sequence of antibody cA2 modified to contain one or more substitutions selected from the group of substitutions L3Q, A9D, I10T, L11S, V13A, Q38H, R39T, I58V, S74T, T77S, V78L, S80A, I83A, D85T, S100G, N103K, L104V, V106I wherein the amino acids are identified using single letter code and the numbering refers to the numerical position of the amino acid where the N-terminal residue equals residue 1;

an accordingly modified antibody V-region additionally comprising a human IgG1 constant region domain and a human kappa constant region domain;

an accordingly modified antibody able to bind TNF alpha an accordingly modified antibody able to provide a protective effect to WEHI164 cells grown in otherwise lethal concentrations of TNF alpha in vitro;

an accordingly modified antibody able to inhibit TNF alpha stimulated production of ICAM-1 in human endothelial cells in vitro;

an accordingly modified antibody able to inhibit TNF alpha stimulated production of IL-6 in human fibroblast cells in vitro;

an accordingly modified antibody comprising one or more V-region domains in which the immunogenic regions have been mapped using a T-cell assay and then modified such that upon re-testing in a T-cell assay the modified protein evokes a stimulation index smaller than the parental (non-modified) molecule;

a modified antibody molecule having the biological activity of monoclonal antibody cA2 and being substantially non-immunogenic or less immunogenic than the non-modified cA2;

a modified antibody molecule having the same biological activity as antibody cA2 when used in vivo;

an accordingly specified antibody molecule, wherein said loss of immunogenicity is achieved by removing one or more T-cell epitopes derived from the originally non-modified molecule;

an accordingly specified antibody molecule, wherein said loss of immunogenicity is achieved by reduction in numbers of MHC allotypes able to bind peptides derived from said molecule;

an accordingly specified antibody molecule, wherein one T-cell epitope is removed;

an accordingly specified antibody molecule, wherein said originally present T-cell epitopes are MHC class II ligands or peptide sequences which show the ability to stimulate or bind T-cells via presentation on MHC class II;

an accordingly specified molecule, wherein said peptide sequences are selected from the group as depicted in FIG. 1;

an accordingly specified molecule, wherein 1-9 amino acid residues, preferably one amino acid residue in any of the originally present T-cell epitopes are altered;

an accordingly specified molecule, wherein the alteration of the amino acid residues is substitution, addition or deletion of originally present amino acid(s) residue(s) by other amino acid residue(s) at specific position(s);

an accordingly specified molecule, wherein, if necessary, additionally further alteration usually by substitution, addition or deletion of specific amino acid(s) is conducted to restore biological activity of said molecule;

an accordingly specified molecule wherein alteration is conducted at one or more residues from any or all of the string of contiguous residues of sequences (A)-(H) as below wherein said sequences are derived from the cA2 antibody V-region sequence domains of the molecule and where using single letter code;

```
A. = GLVQPGGSMKLSCVAS;          (SEQ ID NO:9)

B. = WVAEIRSKSINSA;             (SEQ ID NO:10)

C. = SRDDSKSAVYLQMTDLRT;        (SEQ ID NO:11)

D. = RNYYGSTYDYWGQGTTLTVSS;     (SEQ ID NO:12)
```

-continued

```
E. = DILLTQSPAILSVSPGERVSF;     (SEQ ID NO:13)

F. = HWYQQRTNGSPR;              (SEQ ID NO:14)

G. = LIKYASESMSGIPS;            (SEQ ID NO:15)

H. = DFTLSINTVESEDIADYYCQQ;     (SEQ ID NO:16)
``` a peptide molecule comprising at least 9 consecutive residues from any of the sequences (A)-(H) above;

a peptide molecule of above sharing greater than 90% amino acid identity with any of the peptide sequences derived from (A)-(H);

a peptide molecule of above sharing greater than 80% amino acid identity with any of the peptide sequences derived from (A)-(H) above;

a peptide molecule containing a sequence element identical or substantially homologous with one or more of the sequences (A)-(H) above;

peptide sequences as above able to bind MHC class II;

a pharmaceutical composition comprising any of the peptides or modified peptides of above having the activity of binding to MHC class II a DNA sequence or molecule which codes for any of said specified modified molecules as defined above and below;

a pharmaceutical composition comprising a modified molecule having the biological activity of cA2;

a pharmaceutical composition as defined above and/or in the claims, optionally together with a pharmaceutically acceptable carrier, diluent or excipient;

a method for manufacturing a modified molecule having the biological activity of antibody cA2 as defined above or below and comprising the following steps: (i) determining the amino acid sequence of the polypeptide or part thereof; (ii) identifying one or more potential T-cell epitopes within the amino acid sequence of the protein by any method including determination of the binding of the peptides to MHC molecules using in vitro or in silico techniques or biological assays; (iii) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays; (iv) constructing such sequence variants by recombinant DNA techniques and testing said variants in order to identify one or more variants with desirable properties; and (v) optionally repeating steps (ii)-(iv);

an accordingly specified method, wherein step (iii) is carried out by substitution, addition or deletion of 1-9 amino acid residues in any of the originally present T-cell epitopes;

an accordingly specified method, wherein the alteration is made with reference to an homologous protein sequence and/or in silico modeling techniques;

a peptide sequence consisting of at least 9 consecutive amino acid residues of a 13mer T-cell epitope peptide as specified above and its use for the manufacture of an anti-TNF alpha antibody having substantially no or less immunogenicity than any non-modified molecule and having the biological activity of an anti-TNF alpha antibody when used in vivo.

Reference to "substantially non-immunogenic" or "reduced immunogenic potential" includes reduced immunogenicity compared to a parent antibody, i.e. a non-modified murine or chimeric monoclonal antibody. The term "immunogenicity" includes an ability to provoke, induce or otherwise facilitate a humoral and or T-cell mediated response in a host animal and in particular where the "host animal" is a human.

An important and significant feature of the modified antibodies of the present is that they retain the functional activities of the non-modified or "parental" antibody. It is therefore particularly desired to produce modified antibodies in which all of the beneficial technical features associated with the therapeutic efficacy of the parental non-modified antibody are exhibited. This is pertinent to the contemplated utility of the invention, namely to provide a composition with therapeutic efficacy in a number of important diseases in man including especially rheumatoid arthritis and Crohn's disease and a number of other clinical indications mediated by TNF alpha. Such a therapeutic is a preferred embodiment of the present invention.

Accordingly, the modified antibody of the present exhibits an affinity for its target antigen that is similar to the affinity exhibited by monoclonal antibody cA2. The antibody recognizes TNF alpha but not TNF alpha and is capable of neutralizing TNF alpha activity in a range of in vitro assays. Such assays include cell cytotoxicity, mitogenesis, cytokine induction and induction of adhesion molecules. In addition to neutralizing the biological activity of TNF alpha, the therapeutic efficacy of the parental molecule is believed also to be mediated by the ability of the antibody to induce antibody-dependent cell mediated cytoxicity (ADCC) and is effective at killing cells expressing cell surface bound forms of TNF alpha. The phenomenon of ADCC is mediated by the constant region domain of whole antibody molecules, and the present invention contemplates production of a whole antibody molecules comprising a constant region domain compatible with ADCC induction.

In regard to in vitro assays demonstrating TNF alpha neutralizing activity a number of such assays are described herein as experimental examples and provide evidence that the preferred antibodies of the invention have in vitro potency.

By "antibody" is meant a protein of the immunoglobulin family that is capable of combining, interacting or otherwise associating with an antigen. The term "antigen" is used herein to refer to a substance that is capable of interacting with the antibody and in the context of the present invention is meant to be TNF alpha. The TNF alpha of the present invention is tumor necrosis factor alpha (TNF alpha) and is most preferably human TNF alpha or any TNF alpha representing an antigen for antibody cA2. The TNF alpha may be soluble TNF alpha or membrane associated TNF alpha.

The term "immunoglobulin" is used herein to refer to a protein consisting of one or more polypeptides substantially encoded by immunoglobulin genes. The recognized immunoglobulin genes include the κ, λ, α, γ (IgG1, IgG2, IgG3, IgG4), σ, ε and μ constant region genes and in nature multiple immunoglobulin variable region genes. One natural form of immunoglobulin is a tetramer comprising two identical pairs in which each pair has one light chain and one heavy chain. In each pair the heavy and light chain variable regions together provide the binding surface capable of interacting with the antigen. The term Vh is used herein to refer to the heavy chain variable region, and the term Vk is used herein to refer to the light chain variable region and in this instance in common with numerous monoclonal antibodies the light chain is a "kappa" (κ) type chain.

As used herein, Vh means a polypeptide that is about 110 to 125 amino acid residues in length, the sequence of which corresponds to any of the specified Vh chains herein which in combination with a Vk are capable of binding human TNF alpha. Similarly, Vk means a polypeptide that is about 95-130 amino acid residues in length the sequence of which corresponds to any of the specified Vk chains herein which in combination with a Vh are capable of binding human TNF alpha. Full-length immunoglobulin heavy chains are about 50 kDa molecular weight and are encoded by a Vh gene at the N-terminus and one of the constant region genes (e.g. γ) at the C-terminus. Similarly, full-length light chains are about 25 kDa molecular weight and are encoded by a V-region gene at the N-terminus and a κ or λ constant region gene at the C-terminus.

In addition to whole antibody (tetramers), immunoglobulins may exist in a number of other forms derived by application of recombinant DNA techniques or protein biochemistry. These forms include for example Fv, Fab, Fab' and (Fab)2 molecules and could all contain any of the Vh or Vk sequences of the present invention. A further example may include a "bi-specific" antibody, that is comprising a Vh/Vk combination of the present invention in combination with a second Vh/Vk combination with a different antigen specificity.

The term "T-cell epitope" means according to the understanding of this invention an amino acid sequence which is able to bind MIC class II, able to stimulate T-cells and/or also to bind (without necessarily measurably activating) T-cells in complex with MHC class II.

The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins-that can be formed is practically unlimited. "Alpha carbon (Cα)" is the carbon atom of the carbon-hydrogen (CH) component that is in the peptide chain. A "side chain" is a pendant group to Cα that can comprise a simple or complex group or moiety, having physical dimensions that can vary significantly compared to the dimensions of the peptide.

The general method of the present invention leading to the modified anti-TNF alpha antibody comprises the following steps:
(a) Determining the amino acid sequence of the polypeptide or part thereof
(b) Identifying one or more potential T cell epitopes within the amino acid sequence of the protein by any method including determination of the binding of the peptides to MHC molecules using in vitro or in silico techniques or biological assays.

(c) Designing new sequence variants with one or more amino acids within the identified potential T cell epitopes modified in such a way to substantially reduce or eliminate the activity of the T cell epitope as determined by the binding of the peptides to MHC molecules using in vitro or in silico techniques or biological assays. Such sequence variants are created in such a way to avoid creation of new potential T cell epitopes by the sequence variations unless such new potential T cell epitopes are, in turn, modified in such a way to substantially reduce or eliminate the activity of the T cell epitope.

(d) Constructing such sequence variants by recombinant DNA techniques and testing said variants in order to identify one or more variants with desirable properties.

The identification of potential T-cell epitopes according to step (b) can be carried out according to methods described previously in the art. Suitable methods are disclosed in WO 98/59244; WO 98/52976; WO 00/34317.

Another very efficacious method for identifying T-cell epitopes by calculation is described in the Example 1, which is a preferred embodiment according to this invention. The analysis has been conducted on both the heavy chain and light chain variable region sequences of the anti-TNF alpha antibody.

A further technical approach suitable to the detection of T-cell epitopes is via biological T-cell assay. Such an analysis is described in the Example 2 and is similarly a preferred embodiment according to this invention. Accordingly, the preferred method of biological assay embodied herein comprises the testing of overlapping peptides derived from the heavy chain and light chain variable region sequences of the anti-TNF alpha antibody or alternatively a sub-set of V-region derived peptides such as all or some of those derived by calculation according to the method embodied by Example 1. The synthetic peptides are tested for their ability to evoke a proliferative response in human T-cells cultured in vitro. The proliferative response can be measured by any convenient means but a widely known method as exploited in the present embodiment uses $^3$H-thymidine incorporation. This approach can be conducted using naïve human T-cells taken from healthy donors, and may also be used to test the immunogenicity in vitro of whole protein molecules as well as synthetic peptides. Such a scheme has also been used in the present study (Example 11) to demonstrate to reduced immunogenic potential of a preferred molecule of the invention. The inventors have established that in the operation of a naïve T-cell assay, a stimulation index equal to or greater than 2.0 is a useful measure of induced proliferation. The stimulation index is conventionally derived by division of the proliferation score measured (e.g. counts per minute if using $^3$H-thymidine incorporation) to the test peptide, by the proliferation score measured in cells not contacted with a test (poly)peptide.

In practice a number of variant anti-TNF alpha antibodies may be produced and tested for the desired immune and functional characteristic. It is particularly important when conducting alterations to the protein sequence that the contemplated changes do not introduce new immunogenic epitopes. This event is avoided in practice by re-testing the contemplated sequence for the presence of epitopes and or of MHC class II ligands by any suitable means. One particular means, which is a further embodiment of the invention, is use of an in vitro immunological recall assay involving PBMC preparations cultured in the presence of a priming quantity of test protein (antibody) and re-challenge with either the same test protein or in parallel a modified version of the protein. Such a scheme provides a convenient practical demonstration of a reduced immunogenic potential in a modified protein in the absence of full-scale clinical trials. For most purposes, the variant proteins will be produced by recombinant DNA techniques although other procedures including chemical synthesis may be contemplated.

In a particularly preferred embodiment, the modified antibodies of the present invention are generated by expression of different combinations of the Vh and Vk genes specified herein. The most preferred combination according to the invention comprises the combination Vh5/Vk12. Other combinations have been produced and tested for functional activity in binding TNF alpha and these combinations comprise Vh1/Vk1, Vh1/Vk5, Vh1/Vk8 and Vh8/Vk5. All such combinations of heavy and light chain are encompassed by the present invention.

Accordingly, the present invention provides modified anti-TNF alpha antibodies with reduced immunogenicity in man where the modified antibodies comprise heavy and light chain variable region amino acid sequences selected from SEQ ID No:1/SEQ ID No:5, SEQ ID No:1/SEQ ID No:7, SEQ ID No:1/SEQ ID No:8, SEQ ID No:3/SEQ ID No:6 and SEQ ID No:4/SEQ ID No:7 or combinations of amino acids having at least 70% similarity to one or both amino acid sequences in each of the above listed pairs.

The invention relates to an anti-TNF alpha monoclonal antibody in which substitutions of at least one amino acid residue have been made at positions within the V-regions of the molecule to result in a substantial reduction in activity of or elimination of one or more potential T-cell epitopes from the protein. It is most preferred to provide modified antibody molecules in which amino acid modification (e.g. a substitution) is conducted within the most immunogenic regions of the parent molecule. The major preferred embodiments of the present invention comprise modified antibody molecules for which any of the MHC class II ligands are altered such as to eliminate binding or otherwise reduce the numbers of MHC allotypes to which the peptide can bind. The inventors have discovered and herein disclose, the immunogenic regions of the antibody cA2 molecule in man. It is understood that under certain circumstances additional regions of sequence to those disclosed herein can become immunogenic epitopes, for example in the event of infection with a pathogen expressing a protein or peptide with a similar sequence to that of the present case. In any event, it will be critical for the sequence element to act as an MHC class II ligand and in principle therefore any of the sequences disclosed in FIG. 1 can be considered immunogenic epitopes under the scope of the present invention.

For the elimination of T-cell epitopes, amino acid substitutions are made at appropriate points within the peptide sequence predicted to achieve substantial reduction or elimination of the activity of the T-cell epitope. In practice an appropriate point will preferably equate to an amino acid residue binding within one of the pockets provided within the MHC class II binding groove.

It is most preferred to alter binding within the first pocket of the cleft at the so-called P1 or P1 anchor position of the peptide. The quality of binding interaction between the P1 anchor residue of the peptide and the first pocket of the MHC class II binding groove is recognized as being a major determinant of overall binding affinity for the whole peptide. An appropriate substitution at this position of the peptide will be for a residue less readily accommodated within the pocket, for example, substitution to a more hydrophilic residue.

Amino acid residues in the peptide at positions equating to binding within other pocket regions within the MHC binding cleft are also considered and fall under the scope of the present.

It is understood that single amino acid substitutions within a given potential T cell epitope are the most preferred route by which the epitope may be eliminated. Combinations of substitution within a single epitope may be contemplated and for example can be particularly appropriate where individually defined epitopes are in overlap with each other. Moreover, amino acid substitutions either singly within a given epitope or in combination within a single epitope may be made at positions not equating to the "pocket residues" with respect to the MHC class II binding groove, but at any point within the peptide sequence. All such substitutions fall within the scope of the present.

In as far as this invention relates to modified anti-TNF alpha antibodies, compositions containing such modified antibodies or fragments of modified antibodies and related compositions should be considered within the scope of the invention. The invention therefore contemplates the use and generation of antibody fragments including for example Fv, Fab, Fab' and F(ab')2 fragments. Such fragments may be prepared by standard methods [for example; Coligan et al (*Current Protocols in Immunology*, John Wiley & Sons 1991-1997]. The present invention also contemplates the various recombinant forms of antibody derived molecular species well known in the art. Such species include stabilised Fv fragments including single chain Fv forms (e.g. scFv) comprising a peptide linker joining the Vh and V1 domains, or an Fv stabilised by interchain di-sulphide linkage (dsFv) and which contain additional cysteine residues engineered to facilitate the conjoining of the Vh and V1 domains. Equally, other compositions are familiar in the art and could include species referred to as "minibodies"; and single variable domain "dAbs". Other species still may incorporate means for increasing the valency of the modified antibody V-region domain, i.e. species having multiple antigen binding sites for example by the engineering of dimerisation domains (e.g. "leucine zippers") or also chemical modification strategies.

In another aspect, the present invention relates to nucleic acids encoding modified anti-TNF alpha antibody entities.

In a further aspect the present invention relates to methods for therapeutic treatment of humans using the modified anti-TNF alpha antibody.

The invention will now be illustrated, but not limited, by the following examples. The examples refer to the following drawings:

FIG. 1 provides tables of peptide sequences derived from the V-region domain of anti-TNF alpha antibody cA2 with potential human MHC class II binding activity. FIG. 1A relates to heavy-chain derived sequences. FIG. 1B relates to light-chain derived sequences.

FIG. 2 provides a graph demonstrating the neutralization of TNF alpha induced killing of WEHI cells in vitro using an anti-TNF alpha antibody (Vh5/Vk12) of the invention.

FIG. 3 provides a graph demonstrating the neutralization of TNF alpha stimulated production of ICAM-1 expression in human umbilical vein endothelial cells in vitro using an anti-TNF alpha antibody (Vh5/Vk12) of the invention.

FIG. 4 provides a graph demonstrating the ability of an anti-TNF alpha antibody of the invention (Vh5/Vk12) to compete for binding to TNF alpha with a positive control antibody (infliximab) in an in vitro assay.

FIG. 5 provides a panel of histrograms representing the proliferation response to synthetic peptides in an in vitro naïve T-cell proliferation assay. The data relate to the responses recorded by PBMC from individual donor #4 and are presented for each of peptides CA1-CA75 at both 1 μM and 5 μM concentration. The graphs each plot the Stimulation Index (SI) versus the peptide identification number. SI=CPM Test Peptide/CPM untreated control. Peptide sequences and methods are detailed in Example 2.

FIG. 6 provides proliferative response recorded to each of the 13-mer peptides P1-P15 in an in vitro naïve T-cell proliferation assay. Panel A depicts responses in PBMC from donor #2; panel B depicts responses in PBMC from donor #4. The results are shown for the peptides given at both 1 μM and 5 μM concentration. For both panels, responses with an SI>2.0 are indicated as positive (+) and results with an SI<2.0 are indicated as negative (−).

FIG. 7 shows results of a plate ELISA in which TNF alpha is detected by the modified antibody of the invention (Vh5/Vk12). The binding curve is a plot of the antibody concentration versus optical density at 492 nm (OD492).

FIG. 8 provides amino acid sequences of the modified variable region domains of the anti-TNF alpha antibodies of the invention. Sequences are depicted using single letter code.

FIG. 9 provides a graph demonstrating the neutralization of TNF alpha stimulated production of IL-6 expression in human HS27 fibroblast cells in vitro using an anti-TNF alpha antibody (Vh5/Vk12) of the invention. The negative control (210G12) is a non-TNF alpha binding antibody and the positive control (infliximab) is TNF alpha neutralizing.

FIG. 10 provide a plots depicting the results of an immunogenicity assay using naïve human PBMC cultured in the presence of differing concentrations of modified antibody (Vh5/Vk12) or immunogenic parental antibody (infliximab). The graphs show the results from a responsive donor PBMC (panel A) and non-responsive donor PBMC (panel B). SI=stimulation index

EXAMPLE 1

Identification of Potential MHC class II Ligands in Anti-TNF Alpha VH and VL Protein Sequence by Computational Means.

The scheme for the analysis of peptide sequences with potential to act as MHC class II binding ligands has been described in detail previously [WO 02/069232]. A software tool using this procedure has been developed and applied to the analysis of the anti-TNF alpha antibody V-region domains. In brief, the software was built from a number of elements including a library of model MHC class II molecules, produced to cover a wide number of allotypic variants extant in the human population; a library of peptide backbone structures, produced to encompass theoretical and known backbone conformations. Using these elements, a large data set was generated based on the results of docking each backbone conformation within each model MHC allotype binding groove. The data set encompasses also the best side-chain conformation for all possible amino acids at the given position. The interatomic distances between the peptide side-chains (in the optimum conformation) and the MHC protein are stored in this dataset. A test peptide from the protein of interest is analysed by adding its sequence of side-chains to all backbones and then retrieving the data sets for the optimum side-chain conformations and thus calculating a "peptide score" for each backbone. The best score is selected for display and the process repeated for each of the available MHC model structures. The algorithm has been applied to the analysis of the V-region domains of the anti-TNF alpha antibody cA2. The analysis identifies multiple 13mer peptide sequences which are potential T-cell epitopes by their being predicted MHC class II ligands for one or more allotypes. These peptides are shown in FIG. 1A (heavy-chain derived peptides) and 1B (light-chain derived peptides).

EXAMPLE 2

Identification of T-Cell Epitopes Using Synthetic Peptides and Naïve Human PBMC In Vitro Proliferation Assays.

The interaction between MHC, peptide and T-cell receptor (TCR) provides the structural basis for the antigen specificity of T-cell recognition. T-cell proliferation assays test the binding of peptides to MHC and the recognition of MHC/peptide complexes by the TCR. In vitro T-cell proliferation assays of the present example, involve the stimulation of peripheral blood mononuclear cells (PBMCs), containing antigen presenting cells (APCs) and T-cells. Stimulation is conducted in vitro using synthetic peptide antigens, and in some experiments whole protein antigen. Stimulated T-cell proliferation is measured using $^3$H-thymidine ($^3$H-Thy) and the presence of incorporated $^3$H-Thy assessed using scintillation counting of washed fixed cells.

TABLE 1

Synthetic Peptides

| Peptide # (SEQ ID NO:) | Peptide Sequence |
|---|---|
| Heavy chain peptides | |
| CA1 (17) | EVKLEESGGGLVQPG |
| CA2 (18) | LEESGGGLVQPGGSM |
| CA3 (19) | SGGGLVQPGGSMKLS |
| CA4 (20) | GLVQPGGSMKLSCVA |
| CA5 (21) | QPGGSMKLSCVASGF |
| CA6 (22) | GSMKLSCVASGFIFS |
| CA7 (23) | KLSCVASGFIFSNHW |
| CA8 (24) | CVASGFIFSNHWMNW |
| CA9 (25) | SGFIFSNHWMNWVRQ |
| CA10 (26) | IFSNHWMNWVRQSPE |
| CA11 (27) | NHWMNWVRQSPEKGL |
| CA12 (28) | MNWVRQSPEKGLEWV |
| CA13 (29) | VRQSPEKGLEWVAEI |
| CA14 (30) | SPEKGLEWVAEIRSK |
| CA15 (31) | KGLEWVAEIRSKSIN |
| CA16 (32) | EWVAEIRSKSINSAT |
| CA17 (33) | AEIRSKSINSATHYA |
| CA18 (34) | RSKSINSATHYAESV |
| CA19 (35) | SINSATHYAESVKGR |
| CA20 (36) | SATHYAESVKGRFTI |
| CA21 (37) | HYAESVKGRFTISRD |
| CA22 (38) | ESVKGRFTISRDDSK |
| CA23 (39) | KGRFTISRDDSKSAV |
| CA24 (40) | FTISRDDSKSAVYLQ |
| CA25 (41) | SRDDSKSAVYLQMTD |
| CA26 (42) | DSKSAVYLQMTDLRT |
| CA27 (43) | SAVYLQMTDLRTEDT |
| CA28 (44) | YLQMTDLRTEDTGVY |
| CA29 (45) | MTDLRTEDTGVYYCS |
| CA30 (46) | LRTEDTGVYYCSRNY |
| CA31 (47) | EDTGVYYCSRNYYGS |
| CA32 (48) | GVYYCSRNYYGSTYD |
| CA33 (49) | YCSRNYYGSTYDYWG |
| CA34 (50) | RNYYGSTYDYWGQGT |
| CA35 (51) | YGSTYDYWGQGTTLT |
| CA36 (52) | TYDYWGQGTTLTVSS |
| CA37 (53) | YWGQGTTLTVSSAST |
| CA38 (54) | QGTTLTVSSASTKGP |
| CA39 (55) | TLTVSSASTKGPSVF |
| CA40 (56) | VSSASTKGPSVFPLA |
| Light chain peptides | |
| CA41 (57) | DILLTQSPAILSVSP |
| CA42 (58) | LTQSPAILSVSPGER |

TABLE 1-continued

Synthetic Peptides

| Peptide # (SEQ ID NO:) | Peptide Sequence |
|---|---|
| CA43 (59) | SPAILSVSPGERVSF |
| CA44 (60) | ILSVSPGERVSFSCR |
| CA45 (61) | VSPGERVSFSCRASQ |
| CA46 (62) | GERVSFSCRASQFVG |
| CA47 (63) | VSFSCRASQFVGSSI |
| CA48 (64) | SCRASQFVGSSIHWY |
| CA49 (65) | ASQFVGSSIHWYQQR |
| CA50 (66) | FVGSSIHWYQQRTNG |
| CA51 (67) | SSIHWYQQRTNGSPR |
| CA52 (68) | HWYQQRTNGSPRLLI |
| CA53 (69) | QQRTNGSPRLLIKYA |
| CA54 (70) | TNGSPRLLIKYASES |
| CA55 (71) | SPRLLIKYASESMSG |
| CA56 (72) | LLIKYASESMSGIPS |
| CA57 (73) | KYASESMSGIPSRFS |
| CA58 (74) | SESMSGIPSRFSGSG |
| CA59 (75) | MSGIPSRFSGSGSGT |
| CA60 (76) | IPSRFSGSGSGTDFT |
| CA61 (77) | RFSGSGSGTDFTLSI |
| CA62 (78) | GSGSGTDFTLSINTV |
| CA63 (79) | SGTDFTLSINTVESE |
| CA64 (80) | DFTLSINTVESEDIA |
| CA65 (81) | LSINTVESEDIADYY |
| CA66 (82) | NTVESEDIADYYCQQ |
| CA67 (83) | ESEDIADYYCQQSHS |
| CA68 (84) | DIADYYCQQSHSWPF |
| CA69 (85) | DYYCQQSHSWPFTFG |
| CA70 (86) | CQQSHSWPFTFGSGT |
| CA71 (87) | SHSWPFTFGSGTNLE |
| CA72 (88) | WPFTFGSGTNLEVKR |
| CA73 (89) | TFGSGTNLEVKRTVA |
| CA74 (90) | SGTNLEVKRTVAAPS |
| CA75 (91) | NLEVKRTVAAPSVFI |

Buffy coats from human blood stored for less than 12 hours were obtained from the National Blood Service (Addenbrooks Hospital, Cambridge, UK). Ficoll-paque was obtained from Amersham Pharmacia Biotech (Amersham, UK). Serum free AIM V media for the culture of primary human lymphocytes and containing L-glutamine, 50 µg/ml streptomycin, 10 µg/ml gentomycin and 0.1% human serum albumin was from Gibco-BRL (Paisley, UK). Synthetic peptides were obtained from Eurosequence (Groningen, The Netherlands) and Babraham Technix (Cambridge, UK). Erythrocytes and leukocytes were separated from plasma and platelets by gentle centrifugation of buffy coats. The top phase (containing plasma and platelets) was removed and discarded. Erythrocytes and leukocytes were diluted 1:1 in phosphate buffered saline (PBS) before layering onto 15 ml ficoll-paque (Amersham Pharmacia, Amersham UK). Centrifugation was done according to the manufacturers recommended conditions and PBMCs were harvested from the serum+PBS/ficoll-paque interface. PBMCs were mixed with PBS (1:1) and collected by centrifugation. The supernatant was removed and discarded and the PBMC pellet resuspended in 50 ml PBS. Cells were again pelleted by centrifugation and the PBS supernatant discarded. Cells were resuspended using 50 ml AIM V media and at this point counted and viability assessed using trypan blue dye exclusion. Cells were again collected by centrifugation and the supernatant discarded. Cells were resuspended for cryogenic storage at a density of $3 \times 10^7$ per ml. The storage medium was 90%(v/v) heat inactivated AB human serum (Sigma, Poole, UK) and 10%(v/v) DMSO (Sigma, Poole, UK). Cells were transferred to a regulated freezing container (Sigma) and placed at −70°

C. overnight. When required for use, cells were thawed rapidly in a water bath at 37° C. before transferring to 10 ml pre-warmed AIM V medium.

PBMC were stimulated with protein and peptide antigens in a 96 well flat bottom plate at a density of $2\times10^5$ PBMC per well. PBMC were incubated for 7 days at 37° C. before pulsing with $^3$H-Thy (Amersham-Phamacia, Amersham, UK). For the present study, synthetic peptides (15mers) spanning the entire V-region domains of both the heavy chain and light chain of antibody cA2 were produced. Each peptide overlapped each successive peptide in the sequence by 12 residues, i.e., each peptide incremented from the next in the sequence by 3 residues. The peptide sequences and identification numbers are shown in Table 1. Each peptide was screened individually against PBMC's isolated from 20 naïve donors. Two control peptides C32 (PKYVKQNTLKLAT (SEQ ID NO: 178) and C49 (KVVDQIKKISKPVQH (SEQ ID NO: 179) that have previously been shown to be immunogenic and a potent non-recall antigen KLH were used in each donor assay. Peptides were dissolved in DMSO to a final concentration of 10mM, these stock solutions were then diluted 1/500 in AIM V media (final concentration 20 µM). Peptides were added to a flat bottom 96 well plate to give a final concentration of 2 and 10 µM in a 100 µl. The viability of thawed PBMC's was assessed by trypan blue dye exclusion, cells were then resuspended at a density of $2\times10^6$ cells/ml, and 100 µl ($2\times10^5$ PBMC/well) was transferred to each well containing peptides. Triplicate well cultures were assayed at each peptide concentration. Plates were incubated for 7 days in a humidified atmosphere of 5% $Co_2$ at 37° C. Cells were pulsed for 18-21 hours with 1 µCi $^3$H-Thymidine per well before harvesting onto filter mats. CPM values were determined using a Wallac microplate beta top plate counter (Perkin Elmer). Results were expressed as stimulation indices (SI), where SI=CPM Test Peptide/CPM untreated control.

Mapping T cell epitopes in the cA2 V-region sequences using the naïve T cell proliferation assay resulted in the identification of several immunogenic regions. Peptides with significant stimulation indices in individual donors include for example CA34 (SI=2.22) and CA52 (SI=2.09) amongst others.

The map was refined in sequence regions surrounding the complementarily determining regions (CDRs) for the Vh and the Vk sequences using a further sub-set of 15 different 13-mer peptides (P1-P15) with sequences as below:
P1=KGLEWVAEIRSKS (SEQ ID NO: 92)
P2=EWVAEIRSKSINS (SEQ ID NO: 93)
P3=AEIRSKSINSATH (SEQ ID NO: 94)
P4=KSINSATHYAESV (SEQ ID NO: 95)
P5=TGVYYCSRNYYGS (SEQ ID NO: 96)
P6=STYDYWGQGTTLT (SEQ ID NO: 97)
P7=SQFVGSSIHWYQQ (SEQ ID NO: 98)
P8=QFVGSSIHWYQQR (SEQ ID NO: 99)
P9=SSIHWYQQRTNGS (SEQ ID NO: 100)
P10=HWYQQRTNGSPRL (SEQ ID NO: 101)
P11=PRLLIKYASESMS (SEQ ID NO: 102)
P12=RLLIKYASESMSG (SEQ ID NO: 103)
P13=LLIKYASESMSGI (SEQ ID NO: 104)
P14=IKYASESMSGIPS (SEQ ID NO: 105)
P15=ESMSGIPSRFSGS (SEQ ID NO: 106)

Figure 5:
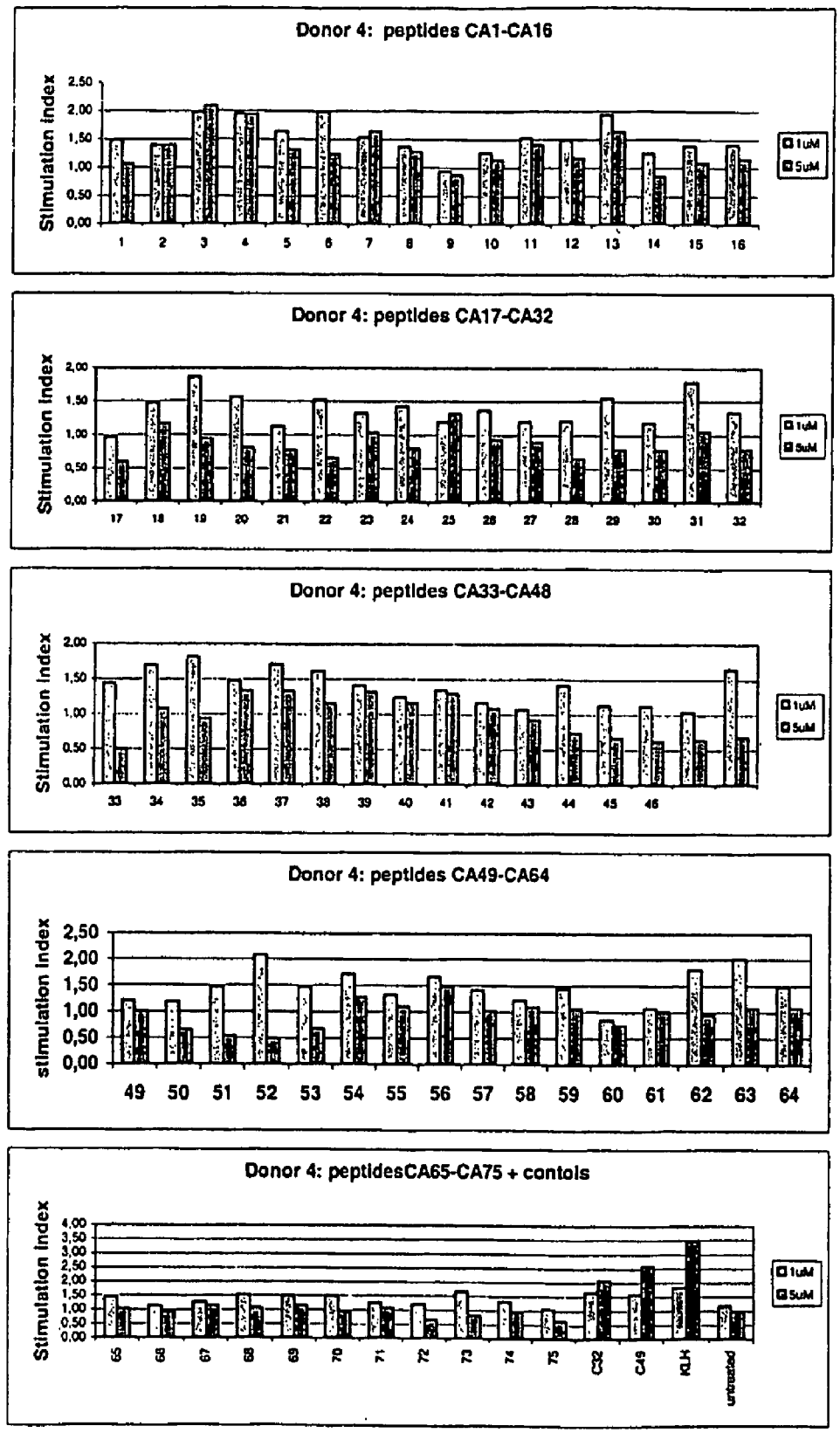

Peptides P1-P7 derive from the Vh chain sequence and peptides P8-P15 derive from the Vk chain sequence. Peptides P1-P15 were screened for their ability to evoke an in vitro proliferative response in a further panel of 10 naïve PBMC preparations encompassing multiple different MHC allotypes as previously. The results of the naïve T-cell proliferation assay from both sets of synthetic peptides and donor panels can be taken together to produce an epitope map of the Vh and Vk chains of the antibody. In general, in compilation of such a map, an SI>1.95 is taken as a positive response. Representative histograms showing the SI to all 15-mer peptides for one responsive donor is given in the accompanying FIG. 5. Exemplary results to the 13-mer peptides P1-P15 are given as FIG. 6.

EXAMPLE 3

Construction of Anti-TNF Alpha Antibody Vh and Vk Genes.

The sequence of the antibody was derived from U.S. Pat. No. 5,656,272. The Variable domain heavy chain (Vh) and the variable domain light chain (Vk) genes were made by gene synthesis. Briefly, a panel of synthetic oligonucleotides were designed and synthesised. The genes were assembled using a ligase chain reaction (LCR) wherein the oligonucleotides featuring complementary ends were allowed to anneal followed by amplification and fill-in using a polymerase chain reaction (PCR). The PCR was driven by addition of an increased concentration of the flanking oligonuclotides to act as primers. The PCR products were assembled into full-length antibody genes by further PCR from vectors containing 5' and 3' immunoglobulin gene flanking regions and sub-cloning into expression vectors for expression of whole antibody. The assembled Vh and Vk genes served as templates for mutagenesis and construction of multiple variant antibody sequences in which T-cell epitopes had been removed.

For assembly of the Vh gene oligonucleotides OL373-OL391 detailed in Table 2 were used. For assembly of the Vk gene oligonucleotides OL392-OL410 detailed in Table 3 were used. For both genes, the LCR was conducted by mixing 20 µl of phosphorylated oligonucleotides with 1 µl Pfu DNA ligase (Stratagene, Amsterdam, NL), 10 µl 10× reaction buffer (supplied with enzyme) and 69 µl water. The reaction mix was placed in a thermal cycler for incubation at 95° C. for 2 minutes followed by 25 cycles of 95° C. for 30 seconds followed by gradual cooling to 60° then incubation at 60° C. for 20 minutes and a final incubation of 3 hours at 60° C. Typically, analysis of a sample of the LCR using 2% agarose gel electrophoresis gave smear with a faint band of correct size just visible. The oligonucleotides in all cases were from MWG-Biotech (Ebersberg, Germany) and were phosphorylated in vitro using T4 DNA kinase (Roche, Lewes, UK) and the suppliers recommended protocol. Following LCR, 5 µL of the reaction was transferred to a PCR mix to amplify the assembled fragment. Oligonucleotides OL373 and OL382 were used to drive the Vh reaction, with oligocucleotides OL392 and OL401 used to drive the Vk reaction. PCR was conducted in a total volume of 50 µl for 15 cycles using Taq DNA polymerase (Roche, Lewes, UK). The reaction was run on a 1% agarose gel and the desired band removed and purified using a Qiagen (Crawley, UK) DNA extraction kit. Products were direct cloned into the pGemT-easy vector (Promega, Southampton, UK) for sequence analysis. Several clones were sequenced until correct clones were obtained. Full-length immunoglobulin genes containing the variable region cassettes produced as described above were assembled using overlapping PCR. Briefly, DNA of the vectors M13-VHPCR1 and M13-VKPCR1 [Orlandi et al (1989), *PNAS*, 89: 3833-7] were used as templates to produce a further two overlapping PCR fragments for each Vh and Vk chains including 5' flanking sequence with the murine heavy chain immunoglobulin promoter and encoding the leader signal peptide and 3' flanking sequence including a splice site and intron sequences. The DNA fragments so produced for each Vh and Vk were combined in a PCR using flanking primers required to obtain full-length DNA sequences. The primer pairs used in these "linking" reactions were oligonucleotides OL411/OL413 and OL414/OL415 for the Vh gene, whereas for the Vk gene, the oligonucleotides OL411/OL412 and OL411/OL401 were used.

The heavy chain gene complete with 5' and 3' flanking sequences was cloned into the expression vector pSVgpt [Reichmann et al (1988) *Nature*, 332: 323] which includes the human IgG1 constant region domain [Takahashi et al (1982) *Cell*, 29: 671] and the gpt gene for selection in mammalian cells. The light chain gene complete with 5' and 3' flanking sequences was cloned into the expression vector pSVhyg [Reichmann et al ibid] in which the gpt gene is replaced by the gene for hygromycin resistance (hyg) and includes a human kappa constant region domain [Heiter et al (1980) *Cell*, 22: 197]. For both vectors, the fully assembled Vh or Vk genes were sub-cloned as HindIII/BamHI fragments purified by gel electrophoresis and handled using well known procedures and reagent systems.

TABLE 2

Synthetic oligonucleotides for Vh

| Name | Sequence | length | SEQ ID NO: |
|---|---|---|---|
| OL 373 | GAAGTGAAGCTGGAGGAGTCTGGAGGCGGCTTGGTGCAAC | 40 | 107 |
| OL 374 | CTGGAGGCTCCATGAAACTCTCCTGTGTTGCCTCTGGATT | 40 | 108 |
| OL 375 | CATTTTCAGTAACCACTGGATGAACTGGGTCCGCCAGTCT | 40 | 109 |
| OL 376 | CCAGAGAAGGGGCTTGAGTGGGTTGCTGAAATTAGATCAA | 40 | 110 |
| OL 377 | AATCGATTAATTCTGCAACACATTATGCGGAGTCTGTGAA | 40 | 111 |
| OL 378 | AGGGAGGTTCACCATCTCAAGAGATGATTCCAAAAGTGCT | 40 | 112 |
| OL 379 | GTGTACCTGCAAATGACCGACCTGAGAACTGAAGACACTG | 40 | 113 |
| OL 380 | GCGTTTATTACTGTTCCAGGAATTACTACGGTAGTACCTA | 40 | 114 |
| OL 381 | CGACTACTGGGGCCAAGGCACCACTCTCACAGTGTCCTCAGG | 42 | 115 |
| OL 382 | CCTGAGGACACTGTGAGAGTGG | 22 | 116 |
| OL 383 | TGCCTTGGCCCCAGTAGTCGTAGGTACTACCGTAGTAATT | 40 | 117 |
| OL 384 | CCTGGAACAGTAATAAACGCCAGTGTCTTCAGTTCTCAGG | 40 | 118 |
| OL 385 | TCGGTCATTTGCAGGTACACAGCACTTTTGGAATCATCTC | 40 | 119 |
| OL 386 | TTGAGATGGTGAACCTCCCTTTCACAGACTCCGCATAATG | 40 | 120 |
| OL 387 | TGTTGCAGAATTAATCGATTTTGATCTAATTCAGCAACC | 40 | 121 |
| OL 388 | CACTCAAGCCCCTTCTCTGGAGACTGGCGGACCCAGTTCA | 40 | 122 |

TABLE 2-continued

Synthetic oligonucleotides for Vh

| Name | Sequence | length | SEQ ID NO: |
|---|---|---|---|
| OL 389 | TCCAGTGGTTACTGAAAATGAATCCAGAGGCAACACAGGA | 40 | 123 |
| OL 390 | GAGTTTCATGGAGCCTCCAGGTTGCACCAAGCCGCCTCCA | 40 | 124 |
| OL 391 | GACTCCTCCAGCTTCACTTC | 20 | 125 |
| OL 413 | AGACTCCTCCAGCTTCACTTCGGAGTGGACACCTGTGGAGAG | 42 | 126 |
| OL 414 | ACCACTCTCACAGTGTCCTCAGGTGAGTCCTTACAACCTCTC | 42 | 127 |
| OL 415 | TTGGGATCCTATAAATCTCTGGCC | 24 | 128 |

TABLE 3

Synthetic oligonucleotides for Vk

| Name | Sequence | length | SEQ ID NO: |
|---|---|---|---|
| OL 392 | GACATCTTGCTGACTCAGTCTCCAGCCATCCTGTCTGTGA | 40 | 129 |
| OL 393 | GTCCAGGAGAAAGAGTCAGTTTCTCCTGCAGGGCCAGTCA | 40 | 130 |
| OL 394 | GTTCGTTGGCTCAAGCATCCACTGGTATCAGCAAAGAACA | 40 | 131 |
| OL 395 | AATGGTTCTCCAAGGCTTCTCATAAAGTATGCTTCTGAGT | 40 | 132 |
| OL 396 | CTATGTCTGGCATCCCTTCTAGATTTAGTGGCAGTGGATC | 40 | 133 |
| OL 397 | AGGGACAGATTTTACTCTTAGCATCAACACTGTGGAGTCT | 40 | 134 |
| OL 398 | GAAGATATTGCAGATTATTACTGTCAACAAGTCATAGCT | 40 | 135 |
| OL 399 | GGCCATTCACGTTCGGCTCGGGGACAAATTTGGAAGTAAA | 40 | 136 |
| OL 400 | ACGTGAGTAGAATTTAAACTTTGCTTCCTCAGTTGGATCCTGGCAGAGTC | 50 | 137 |
| OL 401 | GACTCTGCCAGGATCCAACTGAGGAAGCAA | 30 | 138 |
| OL 402 | AGTTTAAATTCTACTCACGTTTTACTTCCAAATTTGTCCC | 40 | 139 |
| OL 403 | CGAGCCGAACGTGAATGGCCAGCTATGACTTGTTGACAG | 40 | 140 |
| OL 404 | TAATAATCTGCAATATCTTCAGACTCCACAGTGTTGATGC | 40 | 141 |
| OL 405 | TAAGAGTAAAATCTGTCCCTGATCCACTGCCACTAAATCT | 40 | 142 |
| OL 406 | AGAAGGGATGCCAGACATAGACTCAGAAGCATACTTTATG | 40 | 143 |
| OL 407 | AGAAGCCTTGGAGAACCATTTGTTCTTTGCTGATACCAGT | 40 | 144 |

TABLE 3-continued

Synthetic oligonucleotides for Vk

| Name | Sequence | length | SEQ ID NO: |
|---|---|---|---|
| OL 408 | GGATGCTTGAGCCAACGAACTGACTGGCCC TGCAGGAGAA | 40 | 145 |
| OL 409 | ACTGACTCTTTCTCCTGGACTCACAGACAG GATGGCTGGA | 40 | 146 |
| OL 410 | GACTGAGTCAGCAAGATGTC | 20 | 147 |
| OL 411 | TTACGCCAAGCTTATGAATATGCAAATCC | 29 | 148 |
| OL 412 | AGACTGACTCAGCAAGATGTCGGAGTGGAC ACCTGTGGAGAG | 42 | 149 |

TABLE 4

Synthetic oligonucleotides for Vk1 assembly

| Name | Sequence | length | SEQ ID NO: |
|---|---|---|---|
| OL 459 | GACATCCAGCTGACTCAGTCTCCAGACACC TCCTCTGCCA | 40 | 150 |
| OL 460 | CTATGTCTGGCGTGCCTTCTAGATTTAGTG GCAGTGGATC | 40 | 151 |
| OL 461 | AGGGACAGATTTTACTCTTACCATCAACTC CCTGGAGGCC | 40 | 152 |
| OL 462 | GAAGATGCCGCAACCTATTACTGTCAACAA AGTCATAGCT | 40 | 153 |
| OL 463 | GGCCATTCACGTTCGGCTCGGGGACAAATG TGGAAGTAAA | 40 | 154 |
| OL 464 | AGTTTAAATTCTACTCACGTTTTACTTCCA CATTTGTCCC | 40 | 155 |
| OL 465 | TAATAGGTTGCGGCATCTTCGGCCTCCAGG GAGTTGATGG | 40 | 156 |
| OL 466 | AGAAGGCACGCCAGACATAGACTCAGAAGC ATACTTTATG | 40 | 157 |
| OL 467 | ACTGACTCTTTCTCCTGGACTGGCAGAGGA GGTGTCTGGA | 40 | 158 |
| OL 468 | GACTGAGTCAGCTGGATGTC | 20 | 159 |
| OL 469 | AGACTGAGTCAGCTGGATGTCGGAGTGGAC ACCTGTGGAGAG | 42 | 160 |

EXAMPLE 4

Construction of Modified Antibody Vh and Vk Genes.

A modified Vk gene termed Vk1 containing the mutations L3Q, A9D, I10T, L11S, V13A, I58V, S74T, T77S, V78L, S80A, I83A, D85T and L104V was constructed by gene synthesis. Table 4 lists the oligonucleotides listed used in the assembly of Vk1. These oligonucleotides were used, together with OL393, OL394, OL395, OL400, OL401, OL403, OL405, OL407 and OL408 (see example 3 above) in a gene synthesis reaction as to previously. The gene was cloned into the pGEM-T easy vector (Promega) and several clones were sequenced until a correct clone was obtained. Assembly of the full-length immunoglobulin gene and sub-cloning to the expression vector was as per example 3 with the exception that oligonucleotides OL411 and OL469 were used in the linking reaction for the Vk gene.

Additional mutations were introduced in the Vk gene to make further variant Vk genes. These mutations comprised: V19A, Q38H, R39T, S100G, N103K, V106I. The mutagenesis was conducted by PCR using the oligonucleotides listed in table 5. OL768 and OL769, OL770 and OL771 were used in overlap PCR, in combination with OL411 and OL401 (see above). OL648 was used in a single PCR in combination with OL411. The PCR products were cloned into pGEM-T Easy (Promega) and a correct clone identified by sequencing.

Variant Vh genes were also constructed from the wild-type sequence using mutagenesis. Variant Vh genes comprising the substitutions K3Q, E5V, M18L, K19R, V23A, I28T, I51T, I56T, E64D, S79N, A80S, V81L, T86N, D87S, R89K, G94A, T115L and L116V were constructed. These mutations were introduced using the oligonucleotides listed in table 6. Briefly, each set of oligonucleotides was used in overlap PCR, in combination with OL411 and OL415. The PCR products were cloned into pGEM-T Easy (Promega) and a correct clone identified by sequencing.

The Vh or Vk domains were sub-cloned into the expression vectors as HindIII BamHI fragments as previously and variant antibodies expressed according to the method detailed as example 5.

TABLE 5

Synthetic oligonucleotides for Vk mutageneis

| Name | Sequence | length | SEQ ID NO: |
|---|---|---|---|
| OL 648 | GGATCCAACTGAGGAAGCAAAGTTTAAATT CTACTCACGTTTGATTTCCACCTTTGTCCC GCCGCCGAACGTGAATGGCC | 80 | 161 |
| OL 768 | AGTCCAGGAGAAAGAGCCAGTTTCTCCTGC AGG | 33 | 162 |
| OL 769 | CCTGCAGGAGAAACTGGCTCTTTCTCCTGG ACT | 33 | 163 |
| OL 770 | CCACTGGTATCAGCACACAACAAATGGTTC TCCAA | 35 | 164 |
| OL 771 | TTGGAGAACCATTTGTTGTGTGCTGATACC AGTGG | 35 | 165 |

TABLE 6

Synthetic oligonucleotides for Vh mutagenesis

| Name | Sequence | length | SEQ ID NO: |
|---|---|---|---|
| OL 642 | GTCTCAGGGAGCCTCCAGGTTGCACCAAGC CGCCTCCAGACTCCACCAGCTGCACTTCGG AG | 62 | 166 |
| OL 643 | AACCTGGAGGCTCCCTGAGACTCTCCTGTG CTGCCCTCTGGATTCACTTTCAGTAACCACT GG | 62 | 167 |

TABLE 6-continued

Synthetic oligonucleotides for Vh mutagenesis

| Name | Sequence | length | SEQ ID NO: |
|---|---|---|---|
| OL 644 | AGGCTGTTCATTTGCAGGTACAGAGAATTTTTGGAATCATC | 41 | 168 |
| OL 645 | TACCTGCAAATGAACAGCCTGAAAACTGAAGACACTGCCGTTTATTACTG | 50 | 169 |
| OL 654 | GAAACTAGATCAAAATCGACTAATTCTGCA | 30 | 170 |
| OL 655 | ATTAGTCGATTTTGATCTAGTTTCAGCAAC | 30 | 171 |
| OL 656 | CACATTATGCGGACTCTGTGAAAGGG | 26 | 172 |
| OL 657 | CCCTTTCACAGAGTCCGCATAATGTG | 26 | 173 |
| OL 658 | GGCCAAGGCACCCTTGTCACAGTGTCCTCA | 30 | 174 |
| OL 659 | TGAGGACACTGTGACAAGGGTGCCTTGGCC | 30 | 175 |
| OL 899 | GCCAAGGCACCACTGTCACAGTGTCCTCAG | 31 | 176 |
| OL 900 | CCTGAGGACACTGTGACAGTGGTGCCTTGGC | 31 | 177 |

EXAMPLE 5

Expression, Purification and Quantitation of Anti-TNF Alpha Antibodies

The heavy and light chain expression vectors were co-transfected using electroporation into NS/0, a non-immunoglobulin producing mouse myeloma, obtained from the European Collection of Animal Cell Cultures (ECACC). Colonies expressing the gpt to gene were selected in Dulbecco's Modified Eagles Medium (DMEM) supplemented with 10% (v/v) foetal calf serum and antibiotics (all from Gibco, Paisley, UK) and with 0.8 µg/ml mycophenolic acid and 250 µg/ml xanthine (Sigma, Poole, UK).

Production of human antibody by transfected cell clones was measured by ELISA for human IgG [Tempest et al (1991) BioTechnology 9: 266]. Cell lines secreting antibody were expanded and antibody purified by protein A affinity chromatography [Harlow E. Lane D.; in Antibodies a Laboratory Manual, pp 309; Cold Spring Harbor Laboratory Press (1988), NY, USA].

The concentration of the purified antibody was determined using an ELISA detecting the human kappa constant region of the antibodies of interest. A standard concentration curve was determined for a commercial preparation of the therapeutic antibody infliximab (Schering-Plough Ltd, UK) and the standard used to compute the concentration of the test to antibody preparation. The assay was conducted in 96-well plates and all determinations were conducted in duplicate.

For the assay, plates (Dynatech Immulon 2) were coated using 100 µl per well sheep anti-human κ antibody (The Binding Site, Birmingham, UK) diluted 1:250 in carbonate/bicarbonate coating buffer pH9.6 (Sigma, Poole, UK). Coating was conducted for 1 hour at 37° C. and the wells washed 3 times with PBST (PBS with 0.05% Tween 20). The wells were filled with 100 µL of PBST and the dilutions for the control and test antibodies set out. The negative control uses PBST only and no antibody was added. The standard preparation (infliximab) was diluted 1:1000 (v/v) and a doubling dilution series set out across the plate. Doubling dilution series were also set out for the test antibody preparations. The plate was incubated at room temperature for 1 hour and the wells washed as previously. Bound antibody was detected using a peroxidase conjugated sheep ant-human IgG γ chain specific reagent (The Binding Site, Birmingham, UK). This secondary antibody was diluted 1:1000 in PBST and 100 µl added to each well of the plate. The plate was incubated for a further 1 hour at room temperature and washed as previously. Detection was achieved using 100 ul per well "Sigmafast" peroxidase substrate (Sigma, Poole, UK) and the colour development stopped by addition of 40 ul per well 1M sulphuric acid. The optical density was read using a plate reader at 492 nm. A standard curve of antibody concentration versus $A_{492}$ was plotted for the control antibody and the concentration of the test antibody determined by comparison with the standard.

EXAMPLE 6

Protection of TNF Alpha Sensitive Cells in Vitro by TNF Alpha Neutralisation Using Modified Antibodies The ability of anti-TNF alpha antibodies to neutralise the lethal effect of TNF alpha on a cell line grown in vitro was tested using the scheme provided by Galloway [Galloway et al. 1991 J. Immunol. Meth. 140:37-43]. The assay uses the murine fibrosarcoma cell line WEHI164, a line which is very sensitive to the lethal effect of TNF alpha.

For the assay, cells were grown overnight in the presence of a fixed, lethal concentration of TNF alpha and a range of different antibody concentrations. The next day, the metabolic activity of cells was measured as an indication of survival. Antibodies that neutralise TNF alpha confer a protective effect to the cells and thereby a greater metabolic activity is measured in the assay.

WEHI164 were obtained from the European Collection of Animal Cell Cultures (ECACC #. 8702250) and grown in DMEM medium with Glutamax, (Gibco, Paisley, UK), 10% foetal calf serum (Perbio, Chester, UK) and containing antibiotic-mycotic (Gibco). On the day prior to assay, cells are sub-cultured to ensure active proliferation during the subsequent assay period. The assay was conducted in 96 well plates in duplicate for all treatments. Plates were prepared to contain dilutions of control antibody, test antibody and negative control with no antibody. Typically, doubling dilution series of the antibodies were arranged across a plate starting from a concentration of 10 µg/ml antibody in a volume of 50 µl. A stock solution of TNF alpha (PeproTech EC Ltd, London, UK) at 50 µg/ml in medium containing 4 µg/ml of actinomycin was prepared and added to the treatment wells. The TNF alpha solution was mixed by gently tapping the plate and the plate incubated for at least two hours at room temperature before the prepared solutions were transferred to the assay plate containing the cells.

The assay plate was prepared by seeding $2.5 \times 10^4$ cells in 50 µl per well and incubating for at least 1 hour at 37° C., 5% $CO_2$. Following this, 50 µl of the TNF alpha/antibody mixture or control preparation was transferred from the plate used to dilute out the various treatments. The cell and treatment mixtures were mixed by gently tapping the plate and the plate incubated overnight at 37° C. in a humidified atmosphere containing 5% $CO_2$. Next day, the metabolic activity of the cells in each well was assessed using a "CellTiter 96 Aqueous One Solution Cell Proliferation Assay" (Promega, Southampton, UK). Following addition of the assay solution, the plates were incubated for a further 90 minutes and the absorbance of the solutions in each well was read using a plate reader at 492 nm. The absorbance figures are plotted versus antibody concentration. In all assays the positive control preparation was a sample of the therapeutic antibody infliximab (Schering-Plough Ltd, UK), which in this assay consistently demonstrates significant TNF alpha neutralisation at concentrations of less than 0.1 µg/ml. Similarly the modified antibody of the present invention consistently demonstrated a protective effect in this assay equivalent to the positive control preparation. FIG. 2 shows an example plot from this assay.

EXAMPLE 7

Neutralisation of TNF Alpha Stimulated Production of ICAM-1 by Human Endothelial Cells in Vitro.

The ability of anti-TNF alpha antibodies to neutralise TNF alpha stimulated production in human umbilical vein endothelial (HUVE) cells of membrane bound ICAM-1, was tested in an in vitro assay. Briefly, HUVE cells are grown in a 96-well plate in the presence of TNF alpha and varying concentrations of test or control antibody. The quantitative relative expression of membrane bound ICAM-1 is subsequently assessed by cell lysis and an enzyme linked immunoabsorbance assay (ELISA) using a commercially available ICAM-1 detection system.

For the assay, two parallel sets of 96 well plates are prepared. One set, termed the "assay plate", is seeded with cells, the other, termed the "preparation plate", is used to prepare the dilutions of TNF alpha and the test and control antibody solutions. The contents of the preparation plate are ultimately transferred to the assay plate. All assays are conducted in duplicate.

For the assay plate, HUVE cells (Cambrex Bio Science, Wokingham, UK) were seeded at a density of $5 \times 10^4$ cells per well in a volume of 50 µl. The cells were allowed to adhere to the plate by incubation at 37° C., 5% $CO_2$ for at least 2 hours.

For the preparation plate, doubling dilution series of the test and positive control antibody were set out in duplicate across the plate. The starting concentration for the antibodies was 20 µg/ml in a final volume of 100 µl/well. The negative control received no antibody. A solution of 40 ng/ml TNF alpha (PeproTech EC Ltd, London, UK) in medium was prepared and 100 µl per well added to each of the treatment wells on the preparation plate. The plate was mixed by gentle tapping and incubated for 45 minutes at room temperature. Following this incubation, 50 µl from each well of the preparation plate was added to its corresponding well in the assay plate. The assay plate was incubated for 23 hours at 37° C. in a humidified atmosphere containing 5% $CO_2$.

Next day, the medium from all wells was removed and the cells washed once with phosphate buffered saline (PBS). The cells were lysed and the lysate assayed for the presence of ICAM-1. Lysis was achieved by incubation at 4° C. for 45 minutes in 80 µl lysis buffer. Lysis buffer comprised 8.7 µl NaCl, 6.05 g/l Tris 0.5%(v/v) NP40, at pH to 8.0. Lysis buffer also contained protease inhibitors PMSF, iodoacetamide and benzamide at 100 mM concentration and pepsatin A and leupeptin at 50 mM and 5 mM concentrations respectively. These inhibitors were added fresh to the lysis buffer preparation at time of use.

The well contents were mixed using a micropipette before removing the lysate to a fresh round-bottom 96 well plate. The plate was spun to clear precipitated cell debris and the cleared lysate removed to a further fresh 96 well plate for storage, (−20° C.) or immediate assay.

Figure 3:
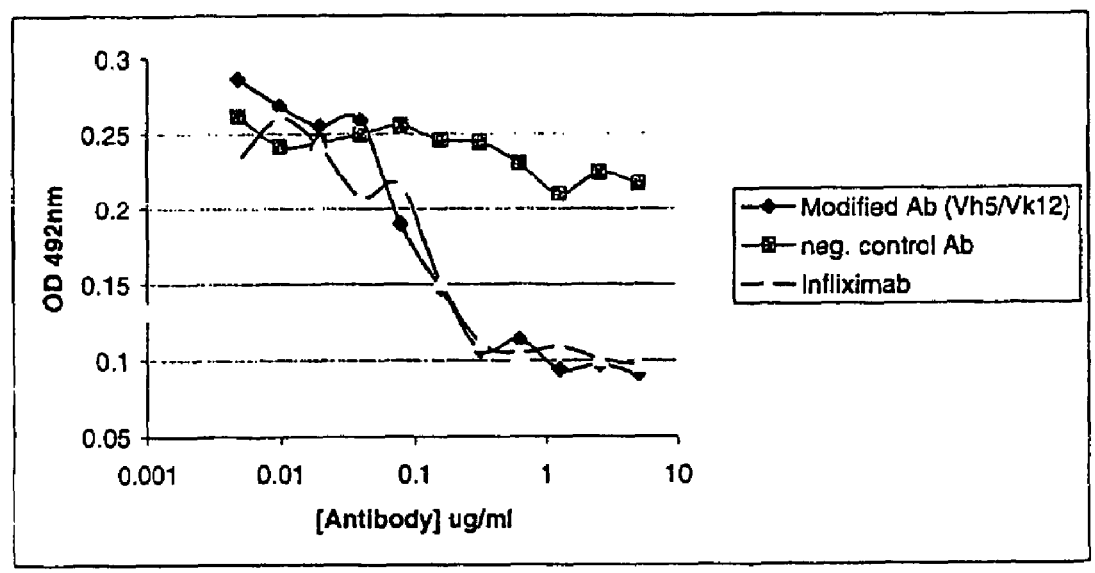

For assay, 20 µl of cleared lysate was analyzed for the presence of solubilized ICAM-1 using a commercial ELISA system (sICAM-1 Module set; Bender Medsystems, Towcester, UK) and conditions recommended by the supplier. The absorbance of the solutions in each well was read using a plate reader at 492 nm. The absorbance figures were plotted versus antibody concentration. In all assays the positive control preparation was a sample of the therapeutic antibody infliximab (Schering-Plough ltd), which in this assay consistently demonstrates significant TNF alpha neutralisation at concentrations of less than 1 g/ml. Similarly the modified antibody of the present invention consistently demonstrates a concentration dependent inhibition ICAM-1 expression equivalent to the positive control preparation. FIG. 3 shows an example plot from this assay.

EXAMPLE 8

Competition Assay of Modified Antibodies for Binding to TNF Alpha

The ability of the modified antibodies of the present invention to compete with the TNF alpha receptor (RII, p75) is measured in a competition ELISA, based on Siegel et al [Siegel et al. (1995) *Cytokine* 7(1):15-25]. ELISA plates were coated with the receptor (TNF alpha RII-Fc) and incubated with a mixture of a fixed amount of biotinylated TNF alpha and a doubling dilution series of the antibody. Binding of TNF alpha to the receptor was measured by colourimetric assay using a Streptavidin-HRP conjugate. The assay was conducted using Immulon 2HB 96 well plates, (Fisher, Loughborough, UK) prepared by coating overnight at 4° C. with 5 µg/ml TNF alpha RII-Fc (R&D Systems, Abingdon, UK) in carbonate coating buffer. A volume 50 µl was applied to each well of the plate. The coated plates were washed at least five times with PBS-0.05% (v/v)Tween 20, (PBS-T) and blocked by addition of a solution of 1% (v/v) BSA in PBS-T and further incubation at room temperature for at least one hour.

During this incubation, a dilution plate was set up in which the test antibody and control reagents were set out. Typically a doubling dilution series starting at a concentration of 50 µg/ml in a final volume of 50 µl/well was used for each test antibody. Controls included non-TNF alpha binding antibody as a negative, and a preparation of clinical grade Infliximab (Schering-Plough ltd, UK) as the positive. Control antibodies were of the same isotype as the test antibodies. Following addition of the antibodies, 50 µl per well of a solution of 50 ng/ml biotin-TNF alpha was added and the plate mixed by gentle tapping. The TNF alpha was a commercially sourced product as previously (Peprotech, London, UK) and biotinylated using EZ link Sulfo-NHS-biotin (Perbio, Tattenhall, UK) and the suppliers recommended protocol.

Figure 4:
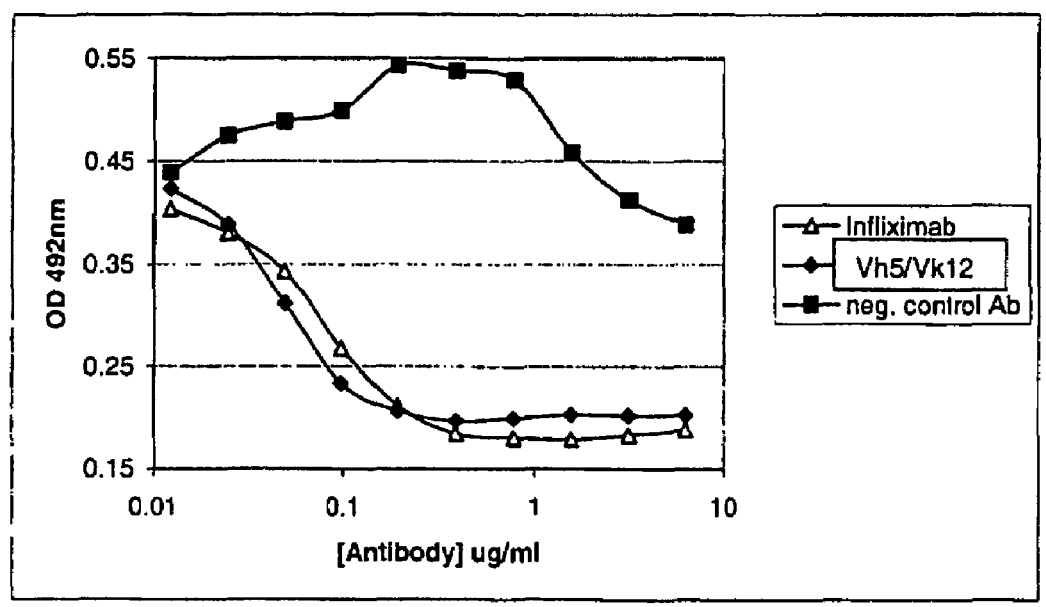

The blocking solution was removed from the assay plate and the plate washed as previously. 50 µl from each well of the dilution plate was added to the relevant well of the assay plate and following mixing, the assay plate incubated for at least one hour at room temperature. Following incubation, the plate was washed and 100 µl of a diluted Streptavidin-HRP (Sigma, Poole, UK) reagent added to all wells of the plate. The plate was further incubated for at least one hour at room temperature and washed as previously. The assay is disclosed using Sigma-fast OPD tablets (Sigma, Poole, UK), 100 µl/well and the colour reaction stopped by adding 50 µl per well 1M Sulphuric acid. The plate was read and the results plotted as antibody concentration versus absorbance at 492 nm. FIG. 4 shows an example plot from this assay. The preferred antibody of the present invention shows a concentration dependent competition curve for TNF alpha binding equivalent to that for the positive control antibody in this assay.

EXAMPLE 9

Inhibition of TNF Alpha Induced Up-Regulation of IL-6 in Hs 27 Cells

Human foreskin fibroblast cells can be induced to produce IL-6 by exposure to TNF alpha. The ability of the modified antibodies of the present invention to block this up-regulation of expression was assessed by co-incubation of the cells with TNF alpha and the test antibodies, followed by a determination of the subsequent IL-6 levels secreted into the medium using a commercially available IL-6 detection system.

For the assay, two parallel sets of 96 well plates are prepared. One set, termed the "assay plate", is seeded with cells, the other, termed the "preparation plate", is used to prepare the dilutions of TNF alpha and the test and control antibody solutions. The contents of the preparation plate are ultimately transferred to the assay plate. All assays are conducted in duplicate.

For the assay plate, human foreskin fibroblast cells Hs 27, obtained from the European Collection of Animal Cell Cultures (ECACC no. 94041901), were seeded at a density of $2 \times 10^4$ cells per well and the cells allowed to adhere to the plate by overnight incubation at 37° C. in a humidified atmosphere containing 5% $CO_2$. The culture medium throughout was DMEM+Glutamax (Gibco, Paisley, UK) containing 10% foetal calf serum (Perbio, Chester, UK) and a conventional antibiotic/mycotic preparation (Gibco).

For the preparation plate, doubling dilution series of the test and positive control antibody were set out in duplicate across the plate. The starting concentration for the antibodies was 1.25 µg/ml in a final volume of 100 µl/well. The negative control received no antibody. A solution of 3 ng/ml TNF alpha (PeproTech EC Ltd., London) was added to all antibody-containing wells, for the control wells with no antibody, an additional 100 µl/well of medium is added. The plate was mixed by gentle tapping and incubated at room temperature for at least 30 minutes.

Medium was removed from the assay plate containing the Hs 27 cells and 10 µl from each well of the preparation plate was transferred to the relevant well of the assay plate. The plate was mixed by gentle tapping and incubated for at least 18 hours at 37° C. in a humidified atmosphere containing 5% $CO_2$. Following incubation, the medium was removed from each well to a fresh U-bottomed 96 well plate for storage at −20° C. or immediate assay.

Figure 9:
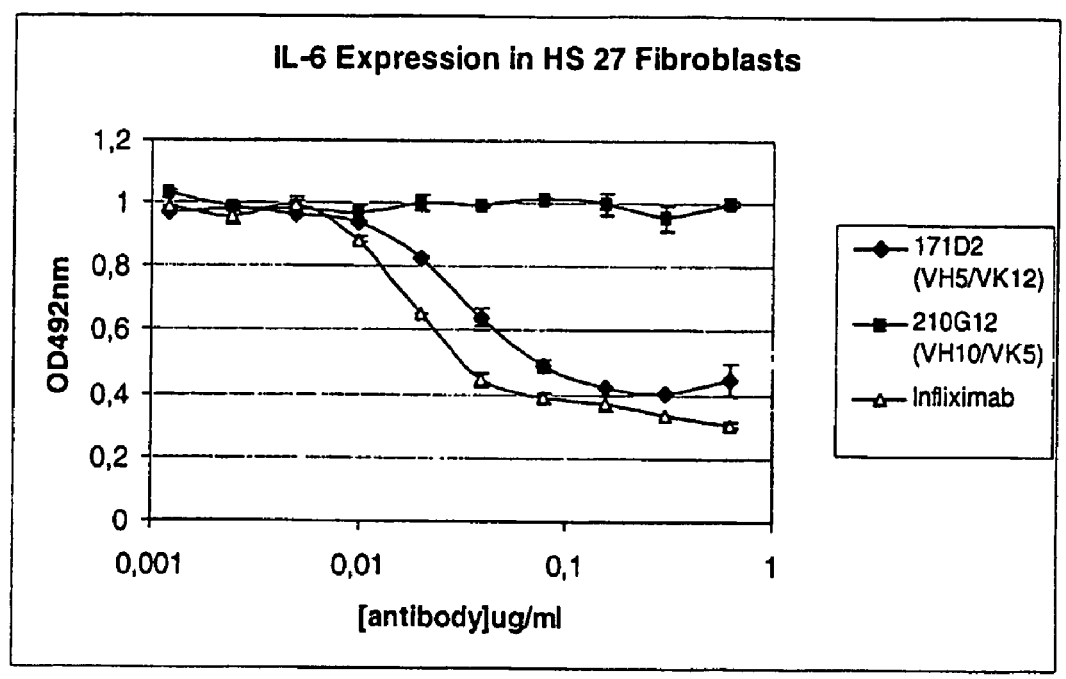

The medium was analysed for the presence of IL-6 using a commercial ELISA system (IL-6 Module set; Bender Medsystems, Towcester, UK) and conditions recommended by the supplier. For assay, 50 µl of medium was diluted 1:15 (v/v). The absorbance of the solutions in each well was read using a plate reader at 492 nm. The absorbance figures were plotted versus antibody concentration. In all assays the positive control preparation was a sample of the therapeutic antibody infliximab (Schering-Plough ltd, UK). The preferred modified antibody of the present invention consistently demonstrates a concentration dependent inhibition IL-6 expression. FIG. 9 shows an example plot from this assay.

EXAMPLE 10

Detection of TNF Alpha

A simple plate ELISA was used to confirm the ability of the modified antibody of the present invention to bind TNF alpha. The assay was conducted in comparison with a preparation of the therapeutic antibody Infliximab (Schering-Plough ltd, UK) as positive control and a non-TNF alpha binding human IgG preparation (Sigma I2511) as a negative control. The assay was conducted using the method detailed below and demonstrates that the preferred composition (Vh5/Vk12) of the present invention has equal efficacy to the control antibody in this assay. A typical binding curve is depicted as FIG. 7. Immulon 2HB 96 well plates, (Fisher, Loughborough, UK) were coated overnight at 4° C. with 2.5 µg/ml TNF alpha (Peprotech, London, UK) in carbonate coating buffer. A volume of 50 µl was applied to each well of the plate. The coated plates were washed three times with PBS-0.05% (v/v)Tween 20, (PBS-T).

Figure 7:
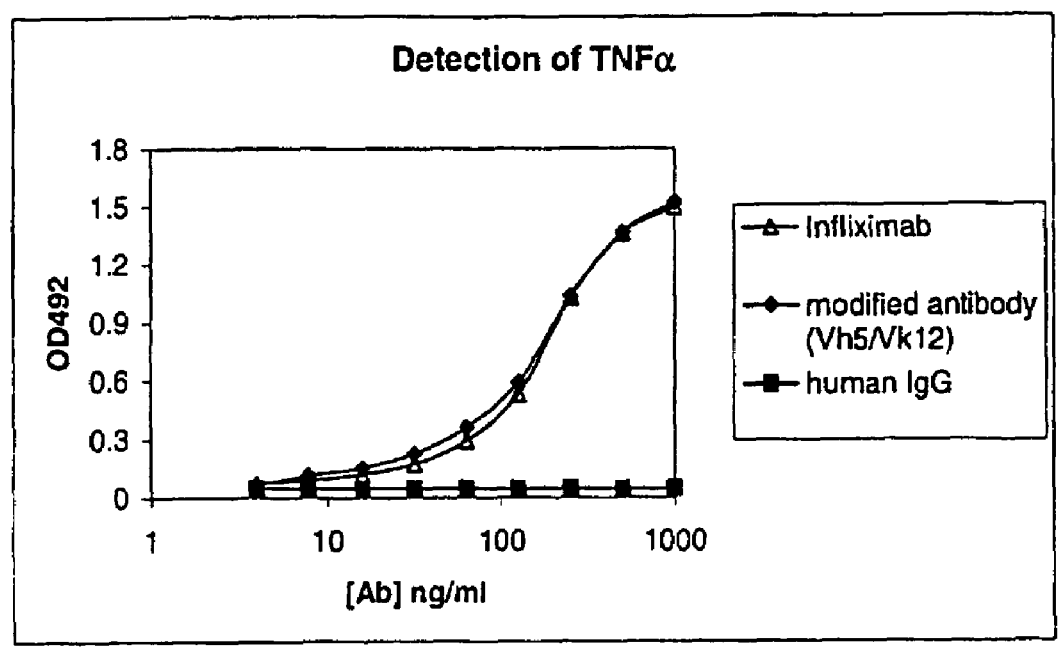

A doubling dilution series of each antibody was prepared and applied in a volume of 100 µl per well, each in duplicate. The highest antibody concentration was 1 µg/ml. Plates were incubated for 1 hour at room temperature and washed as previously with PBST. To detect bound antibody, plates were incubated with a Mouse-anti human IgG-HRP conjugate (Sigma, Poole, UK) preparation diluted 1/1000 in PBST. Incubation was for at least 90 minutes at room temperature. The plates were again washed as previously using PBST and the bound antibody disclosed using 100 µl/well of Sigma-Fast OPD. The color was allowed to develop for 5 minutes and the reaction stopped by addition of 40 µl/well of 1M $H_2SO_4$. The plates were read at 492 nm and the data plotted as concentration of antibody versus the optical density. FIG. 7 shows a representative binding curve indicating functional equivalence in this assay between the modified antibody (Vh5/Vk12) and the positive control.

EXAMPLE 11

Demonstration of Reduced Immunogenic Potential in Modified Anti-TNF Alpha Antibody Using Human PBMC in Vitro Proliferation Assay.

The modified antibody was prepared according to the method of example 5. Positive control (challenge antibody) was clinical grade infliximab (Schering-Plough ltd, UK). For T cell proliferation assays $4 \times 10^6$ PBMC (per well) from healthy donors were incubated with unmodified and modified antibodies in 2 ml bulk cultures (in 24 well plates). Each donor was treated with modified and unmodified antibodies at 5 and 50 µg/ml. In addition an untreated control bulk culture was maintained enabling stimulation indexes to be determined. At days 5, 6, 7 and 8 cells for each bulk culture were gently agitated and 50 µl samples removed in triplicate for determination of the proliferation index. The 50 µl sample aliquots were each transferred to 3 wells of a U-bottom 96 well plate. Fresh AIM V media (130 µl) was added to each of the 96 wells. Cells were pulsed (for 18-21 hours) with 1 µCi [³H]Thymidine per well diluted in a total volume of 20 ul AIM V media. The total volume for each culture was 200 µl. CPM values were collected using a beta-plate reader and the stimulation index for each time point determined as per example 2 above.

Figure 10:
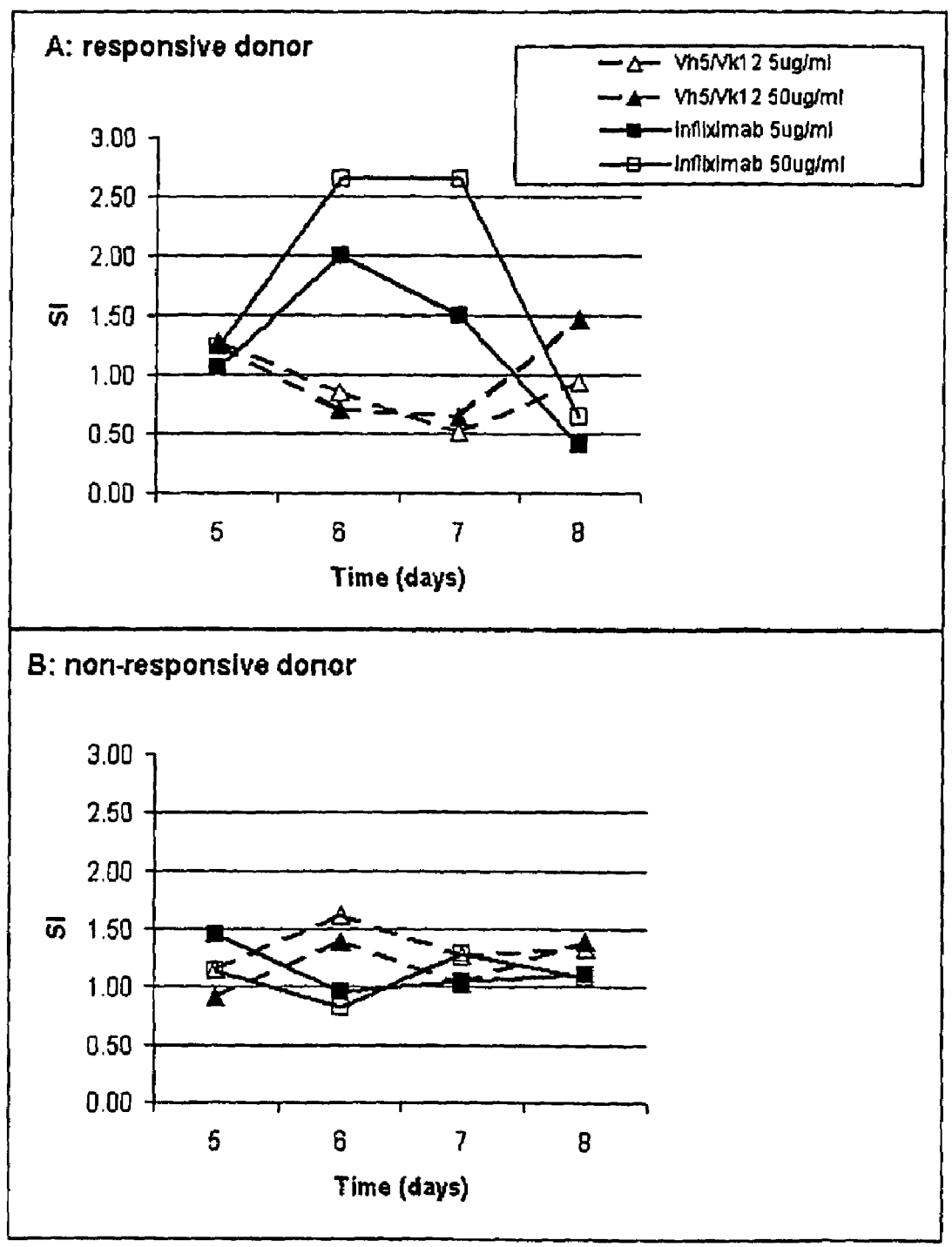

The SI was plotted for each time point and antibody treatment. A significant SI was taken as >2.0. In responsive donors, treatment with infliximab results in a significant proliferative response with a peak at day 7. In the same donors, treatment with the modified antibody composition (Vh5/Vk12) of the present invention does not result in a significant proliferative response. This result indicates a reduced immunogenic potential in the preferred antibody composition of the present compared with the parental antibody. A representative plot from this assay is provided in FIG. 10.

The invention claimed is:

1. A modified monoclonal anti-TNF alpha antibody that is substantially non-immunogenic or less immunogenic than any non-modified antibody having essentially the same biological specificity when used in vivo, and comprising specific amino acid residues having alterations in the V-region of its heavy and/or light chain compared with the non-modified parental antibody, wherein said alterations cause a reduction or an elimination of the number of peptide sequences within said V-region, which act in the parental antibody as MHC class II binding ligands and stimulate T-cells, the parental antibody being infliximab, wherein the modified monoclonal anti-TNF alpha antibody comprises, a heavy chain variable region consisting of SEQ ID NO: 3 and a light chain variable region consisting of SEQ ID NO: 6.

2. The modified antibody of claim 1, wherein the constant region domains derive from human IgG1 and human kappa.

3. The modified antibody according to claim 1, wherein when tested as a whole protein in a biological assay of induced cellular proliferation of human T-cells exhibits a stimulation index smaller than the parental antibody tested in parallel using cells from the same donor wherein said index is taken as the value of cellular proliferation scored following stimulation by the protein and divided by the value of cellular proliferation scored in control cells not in receipt of protein and wherein cellular proliferation is measured by any suitable means.

4. A pharmaceutical composition comprising the modified anti-TNF alpha antibody as defined in claim 1, together with a pharmaceutically acceptable carrier, diluent or excipient.

* * * * *

UNITED STATES PATENT AND TRADEMARK OFFICE
CERTIFICATE OF CORRECTION

PATENT NO. : 7,524,502 B2  Page 1 of 1
APPLICATION NO. : 10/495146
DATED : April 28, 2009
INVENTOR(S) : Koen Hellendoorn et al.

It is certified that error appears in the above-identified patent and that said Letters Patent is hereby corrected as shown below:

Column 2,
Line 7, "Stem et al." should be -- Stern et al. --.
Line 9, "Class H" should be -- Class II --.

Column 12,
Line 26, "MIC" should be -- MHC --.

Column 29,
Line 40, "10 µl" should be -- 100 µl --.

Signed and Sealed this

Fifteenth Day of June, 2010

David J. Kappos
*Director of the United States Patent and Trademark Office*